US009775835B2

(12) United States Patent
Vendeix et al.

(10) Patent No.: US 9,775,835 B2
(45) Date of Patent: Oct. 3, 2017

(54) SMALL MOLECULE INHIBITORS OF VIRAL PROTEIN INTERACTIONS WITH HUMAN T-RNA

(71) Applicant: Sirga Advanced Biopharma, Inc., Research Triangle Park, NC (US)

(72) Inventors: Franck Vendeix, Research Triangle Park, NC (US); Paul F. Agris, Research Triangle Park, NC (US)

(73) Assignee: Sirga Advanced Biopharma, Inc., Research Triangle Park, NC (US)

(*) Notice: Subject to any disclaimer, the term of this patent is extended or adjusted under 35 U.S.C. 154(b) by 0 days.

(21) Appl. No.: 14/419,711

(22) PCT Filed: Aug. 6, 2013

(86) PCT No.: PCT/US2013/053747
§ 371 (c)(1),
(2) Date: Feb. 5, 2015

(87) PCT Pub. No.: WO2014/025749
PCT Pub. Date: Feb. 13, 2014

(65) Prior Publication Data
US 2015/0190384 A1 Jul. 9, 2015

Related U.S. Application Data

(60) Provisional application No. 61/680,064, filed on Aug. 6, 2012.

(51) Int. Cl.
*A61K 31/44* (2006.01)
*A61K 31/445* (2006.01)
(Continued)

(52) U.S. Cl.
CPC .......... *A61K 31/445* (2013.01); *A61K 31/085* (2013.01); *A61K 31/136* (2013.01);
(Continued)

(58) Field of Classification Search
CPC .................................................. A61K 31/4745
(Continued)

(56) References Cited

U.S. PATENT DOCUMENTS 5,827,935 A * 10/1998 Rossi ..................... C12Q 1/703
435/5
6,303,604 B1 10/2001 Moschel
(Continued)

FOREIGN PATENT DOCUMENTS

GB 2265373 A 10/1998

OTHER PUBLICATIONS

Openshaw et al. "Synthesis of emetine and related compounds. III. REaction of some isoquinoline derivatives with acrylonitrile," Journal of the Chemical Society, 1961, pp. 4939-4944.*
(Continued)

*Primary Examiner* — Shengjun Wang
(74) *Attorney, Agent, or Firm* — Cheryl H. Agris; Agris & von Natzmer, LLP

(57) ABSTRACT

Disclosed herein are compounds, compositions and methods of their use to treat HIV/AIDS disease in a subject in need thereof, wherein the compositions comprise small molecule inhibitors that inhibit viral preparation or viral recruitment of human tRNA3Lys.

10 Claims, 21 Drawing Sheets

HIV life Cycle

(51) Int. Cl.
| | |
|---|---|
| A61K 31/085 | (2006.01) |
| A61K 31/136 | (2006.01) |
| A61K 31/18 | (2006.01) |
| A61K 31/222 | (2006.01) |
| A61K 31/37 | (2006.01) |
| A61K 31/427 | (2006.01) |
| A61K 31/428 | (2006.01) |
| A61K 31/4453 | (2006.01) |
| A61K 31/4468 | (2006.01) |
| A61K 31/47 | (2006.01) |
| A61K 31/473 | (2006.01) |
| A61K 31/4745 | (2006.01) |
| A61K 31/519 | (2006.01) |
| A61K 31/53 | (2006.01) |
| A61K 31/63 | (2006.01) |
| A61K 31/517 | (2006.01) |
| A61K 31/5377 | (2006.01) |
| A61K 31/55 | (2006.01) |

(52) U.S. Cl.
CPC ............ *A61K 31/18* (2013.01); *A61K 31/222* (2013.01); *A61K 31/37* (2013.01); *A61K 31/427* (2013.01); *A61K 31/428* (2013.01); *A61K 31/44* (2013.01); *A61K 31/4453* (2013.01); *A61K 31/4468* (2013.01); *A61K 31/47* (2013.01); *A61K 31/473* (2013.01); *A61K 31/4745* (2013.01); *A61K 31/517* (2013.01); *A61K 31/519* (2013.01); *A61K 31/53* (2013.01); *A61K 31/5377* (2013.01); *A61K 31/55* (2013.01); *A61K 31/63* (2013.01)

(58) Field of Classification Search
USPC ........................................................ 514/294
See application file for complete search history.

(56) References Cited

U.S. PATENT DOCUMENTS

| 6,417,393 | B1 | 7/2002 | Christophersen |
| 7,208,497 | B2 | 4/2007 | Dorwald |
| 2008/0200467 | A1 | 8/2008 | Patel |
| 2008/0207760 | A1 | 8/2008 | Huang |
| 2011/0118300 | A1 | 5/2011 | Harris |

OTHER PUBLICATIONS

WO. Appln. No. PCT/US14/47859 (published as WO 2015013431 A1 and counterpart to instant application), International Search Report, dated Feb. 7, 2014.
WO Appln. No. PCT/US14/47859 (published as WO 2015013431 A1 and counterpart to instant application), International Preliminary Report on Patentability, dated Dec. 9, 2014.
PubChem search of 18200-3 (9,10-dimethoxy-4-oxo-3,4,6,7-tetrahydro-2H-pyrido[2,1-a]isoquinoline-1-carbonitrile) at https://pubchem.ncbi.nlm.nih.gov/compound/977094#section=Top, accessed Jun. 12, 2016.
Ackley et al., (2004) "Metabolic Stability Assessed by Liver Microsomes and Hepatocytes," Optimization in Drug Discovery 10:151-162.
Adamson et al., (2008) "Recent Progress in Antiretrovirals—Lessons from Resistance," Drug Discov. Today 13:424-432.
Adamson et al., (2009) "Anti-HIV-1 Therapeutics: From FDA-approved Drugs to Hypothetical Future Targets", Mol Intervention, 9:70-74.
Agris et al., (1995). "Site-selected Introduction of Modified Purine and Pyrimidine Ribonucleosides into RNA by Automated Phosphoramidite Chemistry," Biochimie 77:125-134.
Agris et al., (1999) "Experimental Models of Protein-RNA Interaction: Isolation and Analyses of tRNAPhe and U1 snRNA-Binding Peptides from Bacteriophage Display Libraries," J. Protein Chem. 18:425-435.
Arts et al., (1996) "Initiation of (−) Strand DNA Synthesis from tRNA3Lys on Lentiviral RNAs: Implications of Specific HIV-1 RNA-tRNA3Lys Interactions Inhibiting Primer Utilization by Retroviral Reverse Transcriptases", PNAS 93:10063-10068.
Beuning et al., (1999) "Transfer RNA Recognition by Aminoacyl-tRNA Synthetases," Biopolymers 52:1-28.
Brule et al., (2000) "In Vitro Evidence for the Interaction of tRNA3lys with U3 during the First Strand Transfer of HIV-1 Reverse Transcription", Nucleic Acids Res. 28:634-640.
Cohen (2010) "New HIV Infections Drop, but Treatment Demands Rise", Science 330:1301.
Diaz et al., (2004) "The [3H]dofetilide Binding Assay is a Predictive Screening Tool for hERG Blockade and Proarrhythmia: Comparison of Intact Cell and Membrane Preparations and Effects of Altering [K+]o", J. Pharmacol. Toxicol. Meth. 50:187-199.
Eshete et al., (2007) "Specificity of Phage Display Selected Peptides for Modified Anticodon Stem and Loop Domains of tRNA", The Protein J. 26:61-73.
Frugier et al., (1997) "Subtle Atomic Group Discrimination in the RNA Minor Groove" PNAS 94:11291-11294.
Graham et al., (2011) "Functional Recognition of the Modified Human tRNALys3UUU Anticodon Domain by HIV's Nucleocapsid Protein and a Peptide Mimic", J. Mol. Biol. 410(4):698-715.
Grate et al., (1997) "Role REVersal: Understanding How RRE RNA Binds its Peptide Ligand", Structure 5:7-11.
Greene et al., (2008) "Novel targets for HIV therapy," Antiviral Res, 80:251-265.
Jochmans (2008) "Novel HIV-1 Reverse Transcriptase Inhibitors". Virus Res. 134:171-185.
Kaushik et al., (2001) "Destabilization of tRNA3Lys from the Primer-binding Site of HIV-1 Genome by Anti-A Loop Polyamide Nucleotide Analog," Nucleic Acids Res. 29:5099-51 06.
Kleiman et al., (2004) "The tRNALys packaging complex in HIV-1," Int. J. Biochem. Cell Biol. 36:1776-1786.
Kleiman et al., (2010) "Formation of the tRNALys Packaging Complex in HIV-1," FEBS Lett. 584:359-365.
Lanchy et al., (1996) "Structural and Functional Evidence That Initiation and Elongation of HIV-I Reverse Transcription are Distinct Processes," Biochimie, 78:1087-1096.
Lehmann et al., (1998) "The Human Orphan Nuclear Receptor PXR Is Activated by Compounds That Regulate CYP3A4 Gene Expression and Cause Drug Interactions," J Clin. Invest. 102:1016-1023.
Li (2001) "Screening for Human ADME/Tox Drug Properties in Drug Discovery", Drug Discov. Today 6: 357-366.
Lipinski et al., (2001) "Experimental and Computational Approaches to Estimate Solubility and Permeability in Drug Discovery and Development Settings," Adv. Drug Deliv. Rev. 46:3-26.
Long et al., (1999) "Characterization of the Solution Conformations of Unbound and Tat Peptide-Bound Forms of HIV-1 TAR RNA", Biochemistry 38:10059-10069.
Marquet et al. (1995) "tRNAs as Primer of Reverse Transcriptases", Biochimie 77:113-124.
Mayer et al., (1999) "CharaSaturation Transfer Difference NMR Spectroscopy," Angew. Chem. Int. Ed 38:1784-1788.
Meyer et al., (2004) "Saturation Transfer Difference NMR Spectroscopy for Identifying Ligand Epitopes and Binding Specificities," in Leucocyte Trafficking : The Role of Fucosyltransferases and Selectins 9:149-167.
Miller et al., (2000) "Fluorometric High-Throughput Screening for Inhibitors of Cytochrome P450," Ann. N. Y. Acad. Sci. 919:26-32.
Mitsuya et al., (2008) "Development of protease inhibitors and the fight with drug-resistant HIV-1 variants," Adv. Pharmacol. 56:169-197.
Moore-Rigdon et al., (2005) "Preferences for the Selection of Unique tRNA Primers Revealed from Analysis of HIV-1 Replication in Peripheral Blood Mononuclear Cells," Retrovirology 2: 21.
Mucha et al., (2001) "Anticodon Domain Methylated Nucleosides of Yeast tRNAPhe Are Significant Recognition Determinants in the Binding of a Phage Display Selected Peptide," Biochemistry 40:14191-14199.

(56) References Cited

OTHER PUBLICATIONS

Mucha et al., (2002) "Interaction of RNA with Phage Display Selected Peptides Analyzed by Capillary Electrophoresis Mobility Shift Assay," RNA 8:698-704.

Mucha et al., (2003) "Using Capillary Electrophoresis to Study Methylation Effect on RNA-peptide Interaction," Acta Biochim. Pol. 50:857-864.

Mucha et al., (2003) "Sequence-Altered Peptide Adopts Optimum Conformation for Modification-Dependent Binding of the Yeast tRNAPhe Anticodon Domain Protein," Protein J 23:33-38.

Palm et al., (1991) "Polar Molecule Surface Properties Predict the Intestinal Absorption of Drugs in Humans," Pharm. Res. 14:568-571.

Rankovic et al., (2010) "Lead Generation Approaches in Drug Discovery," Approaches in Drug Discovery, John Wiley & Sons, Inc.

Rodrigues et al., (1997), "Application of Human Liver Microsomes in Metabolism-Based Drug-Drug Interactions: In vitro-In vivo Correlations and the Abbott Laboratories Experience," Adv. Pharmacol., 43:65-101.

Sanderson et al., (1991) "Computer Prediction of Possible Toxic Action from Chemical Structure; The DEREK System," Hum. Exp. Toxicol. 10:261-273.

Schultz et al., (2008) "RNase H Activity: Structure, Specificity, and Function in Reverse Transcription," Virus Res. 134:86-103.

Simon et al., (2006) "HIV/AIDS Epidemiology, Pathogenesis, Prevention, and Treatment," Lancet 368:489-504.

Stroud et al., (2007) Computational and Structural Approaches to Drug Discovery Ligand-Protein Interactions, RSC publishing.

Sundaram et al., (2000) "Hypermodified Nucleosides in the Anticodon of tRNALys Stabilize a Canonical U-Turn Structure," Biochemistry 39:12575-12584.

Trott et al., (2010) "AutoDock Vina: Improving the Speed and Accuracy of Docking with a New Scoring Function, Efficient Optimization and Multithreading," J. Comput. Chem. 31: 455-461.

Vendeix et al., (2012) "Human tRNALys3 UUU is Pre-Structured by Natural Modifications for Cognate and Wobble Codon Binding through Keto-EnolTautomerism," J. Mol. Biol. 416:467-85.

Volpe (2008) "Variability in Caco-2 and MDCK Cell-Based Intestinal Permeability Assays," J. Pharm. Sci. 97:712-725.

Warrilow et al., (2010) "Strand Transfer and Elongation of HIV-1 Reverse Transcription Is Facilitated by Cell Factors In Vitro," PLOS. One 5: e13229.

Weiss et al., (1998) "RNA Recognition by Arginine-Rich Peptide," Biopolymers 48:167-180.

Wible et al., (2005) "HERG-Lite: A Novel Comprehensive High-Throughput Screen for Drug-Induced hERG Risk," J. Pharmacol. Toxicol. Meth. 52:136-145.

Ye et al., (1999) "RNA Architecture Dictates the Conformations of a Bound Peptide," Chem. Biol. 6:657-669.

\* cited by examiner

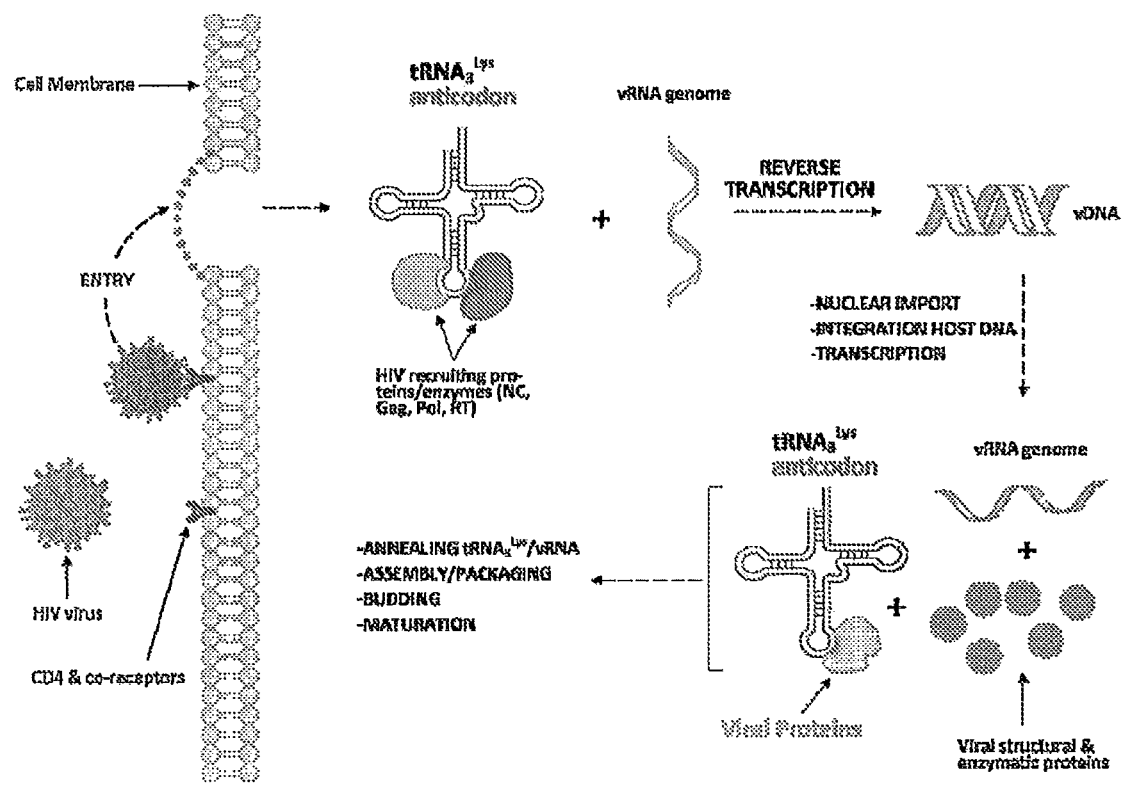
Fig. 1: HIV life Cycle

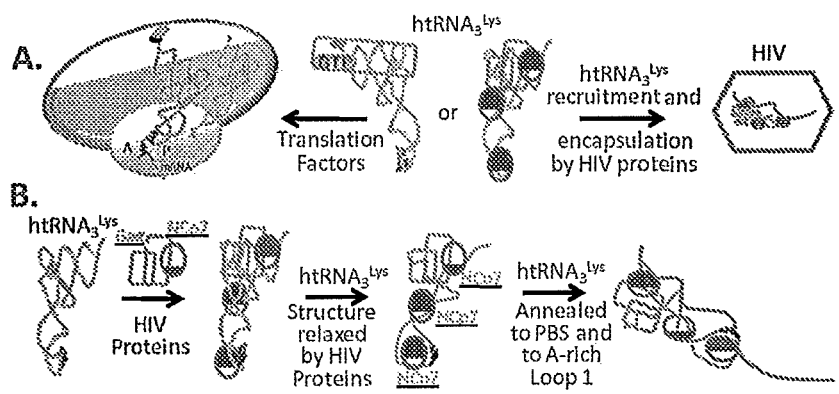

Fig. 2: Schematics of interaction of HIV proteins with htRNA$_3^{Lys}$. HIV recruits human tRNA$_3^{Lys}$ as primer of RT. A. HIV recruits tRNA$_3^{Lys}$ in competing with protein synthesis. B. HIV proteins, including nucleocapsid protein NCp7, specifically recognize tRNA$_3^{Lys}$. NCp7 binding relaxes the tRNA's conformation (Graham et al., 2011). The relaxed tRNA$_3^{Lys}$ conformation is annealed to the HIV genomic RNA. Peptides mimic this binding and denaturation (Graham et al., 2011).

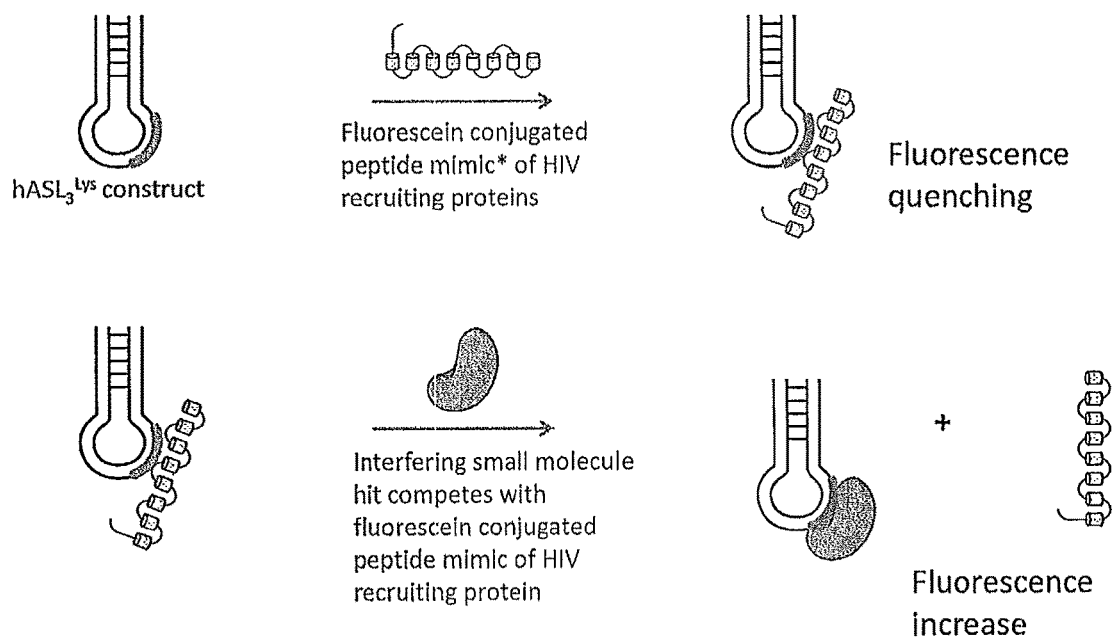
Fig. 3: Schematic of Fluorescence Assay.

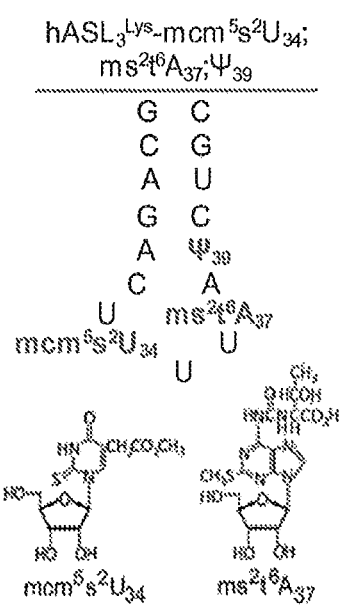
Fig. 4: Sequence and secondary structure of hASL$_3^{Lys}$

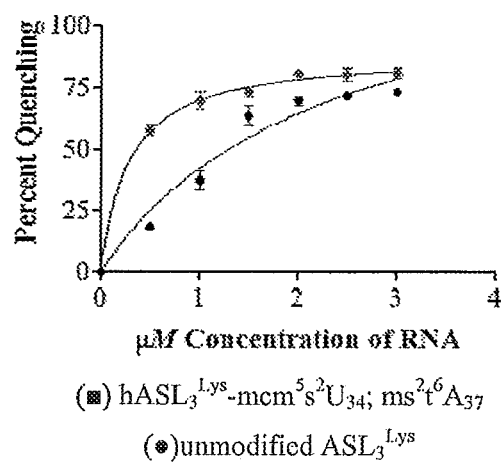
(■) hASL$_3^{Lys}$-mcm$^5$s$^2$U$_{34}$; ms$^2$t$^6$A$_{37}$
(●)unmodified ASL$_3^{Lys}$
Fig. 5: Fluorescence quenching of NCp7's one tryptophan through binding of hASL$_3^{Lys}$-mcm$^5$s$^2$U$_{34}$; ms$^2$t$^6$A$_{37}$ or unmodified ASL$_3^{Lys}$

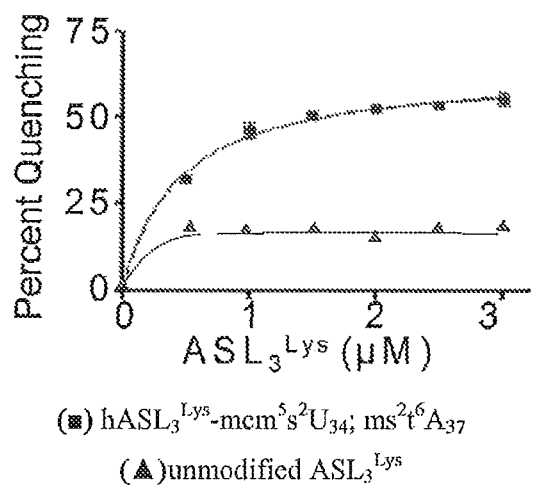
Fig. 6: Fluorescence quenching of FITC conjugated peptide #6 (P6) through binding of hASL$_3^{Lys}$-mcm$^5$s$^2$U$_{34}$; ms$^2$t$^6$A$_{37}$ or unmodified ASL$_3^{Lys}$.

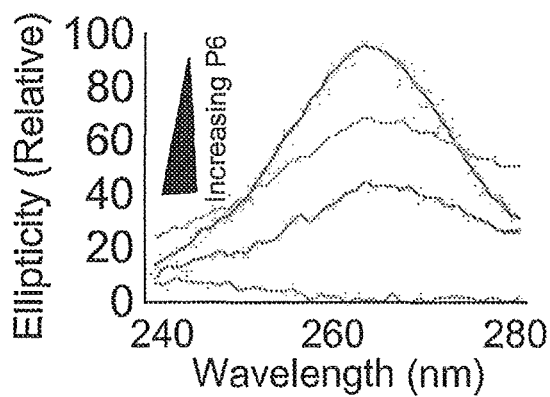
Fig. 7: Circular Dichroism (CD) spectra of NCp7 and P6 complexes with hASL$_3^{Lys}$-mcm$^5$s$^2$U$_{34}$; ms$^2$t$^6$A$_{37}$.P6 unfolds hASL$_3^{Lys}$-mcm$^5$s$^2$U$_{34}$;ms$^2$t$^6$A$_{37}$. CD ellipticity of hASL$_3^{Lys}$ spectra decrease with increasing P6 (P6/ASL = 0/1; 1/1; 3/1; 6/1). NCp7 exhibits similar results. Proteins have no ellipticity from 240-280 nm (Graham et al., 2011).

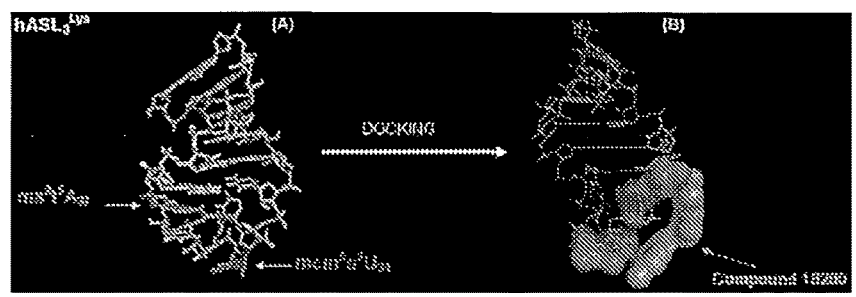

Fig. 8: Docking experiment between hASL$_3^{Lys}$ and small molecules. (A) The NMR structure of the doubly modified hASL$_3^{Lys}$ used to conduct the docking experiments. The modifications mcm$^5$s$^2$U$_{34}$ and ms$^2$t$_6$A$_{37}$ at positions 34 and 37 in the loop are in red. (B) Results of the docking experiment showing the interactions between one molecule hit 18200 (green), and the functional groups of the modifications (the targets, red).

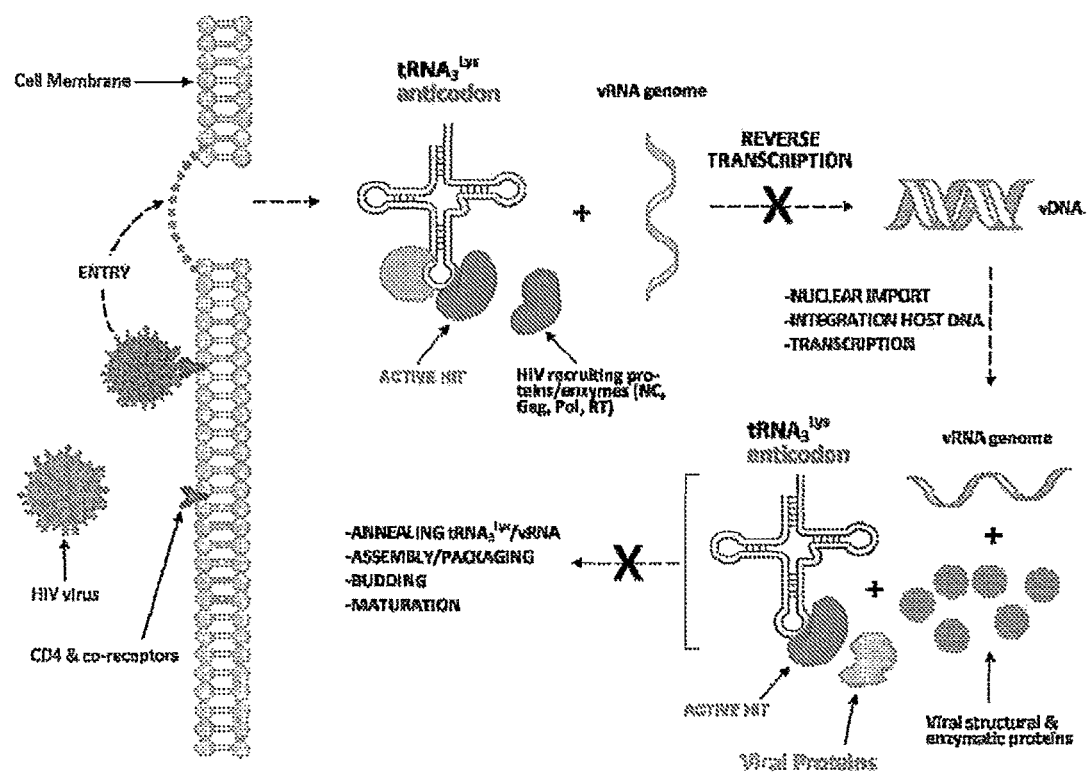
Fig. 9: Schematic of Cell-Based Assay: Active Hit of Interferring small molecule competes with HIV recruiting proteins for binding to tRNA$^{Lys3}$.

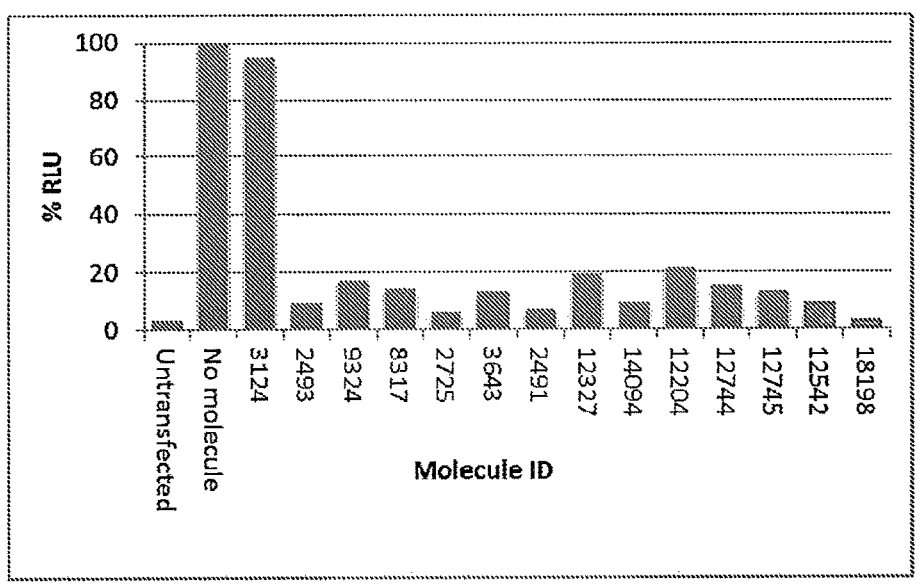

Fig. 10: Level 1 Screen with HIV cell based assay of the 1000 selected small molecules screened at their highest non-toxic concentrations, a number of molecules had noticeable inhibitory activity against HIV propagation. The inhibition is observed for molecules having a Relative Luminescence Unit (RLU) comparable to that of untransfected cells. Experiments were run in triplicate.

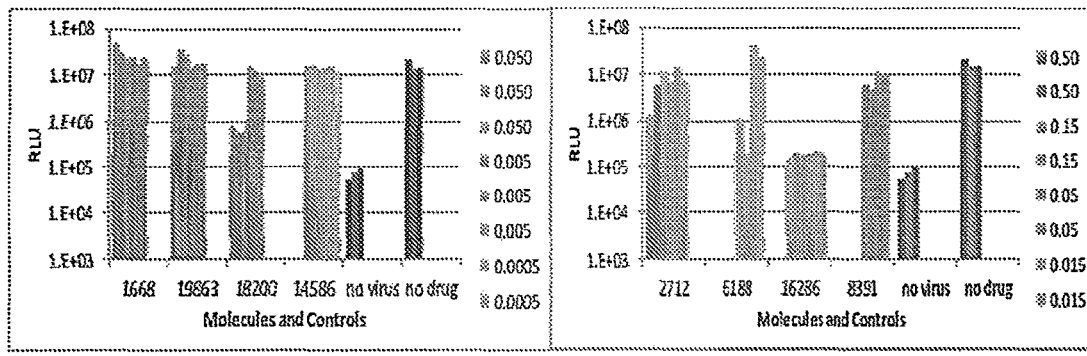

Fig. 11. Level 2 Screen using HIV cell based assay of the selected small molecules screened in a concentration dependent manner. Compounds 18200, 6188, 16286 and 8391 showed noticeable inhibitory activity against HIV propagation. A number of bars are missing due to the toxicity of certain compounds a high concentration. The values showed on the right side of the graph represent the different concentrations tested.in % (0.5% = 0.05 mM).

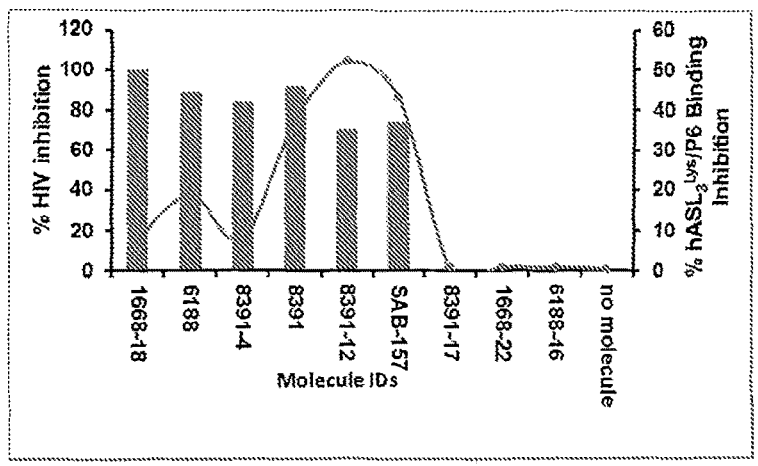

Fig. 12C.

Figs. 12 A, B and C: Small molecules screening using the MBS and HIV cell based assays. (Sh$t\ —) % HIV inhibition resulting from the HIV cell based assay. (RN1, ---) % inhibitions of the complex hASL$^L$ys/P6 by small molecules resulting from the MBS assay. This result also shows initial SAR of the identified active small molecule hits. Molecules 8391-17, 1668-22 and 6188-16, for example, showed no inhibition in both assays.

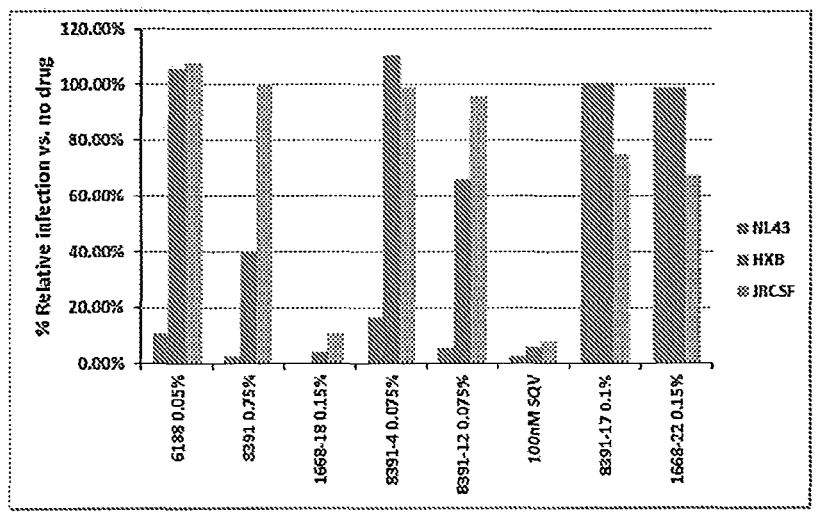
Fig. 13: Small Molecule effects on NL43, HXB (laboratory) and JRC-SF (patient) strains of HIV.

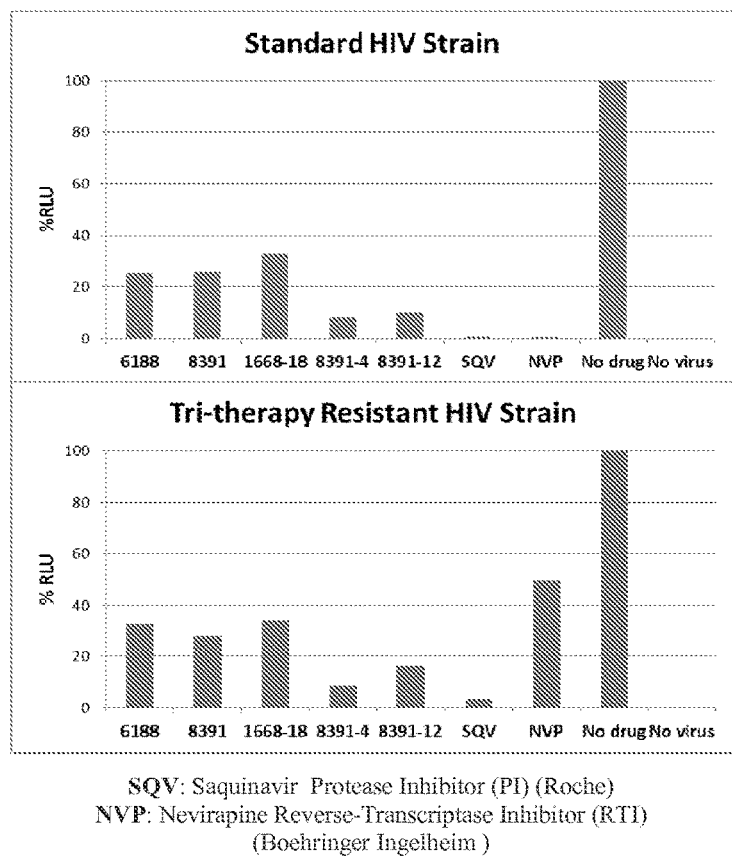
Fig. 14: Effect of Small Molecule Hits on Cell Culture Viral Propagation Compared to Saquinavir and Nevirapine with a Tri-therapy Resistant Strain.

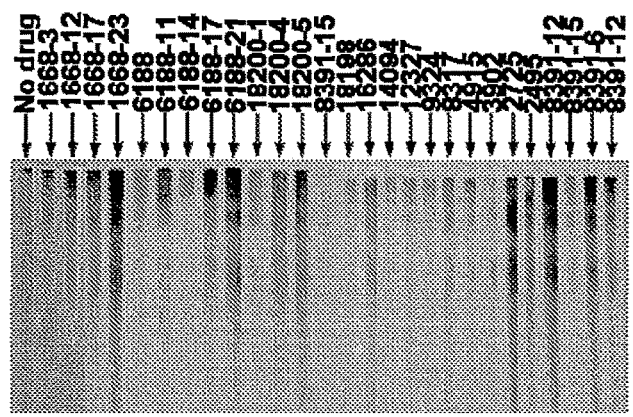

Fig. 15: Acrylamide gel showing the specificity of the identified bioactive small molecules. Lane 1 contains no drug; lanes 2-28 contain the identified active small molecules. Fainted lanes compared to 1 (no drug) are indicative of molecules that bind htRNA$_3^{Lys}$ specifically in the presence of non-specific nucleic acids, and consequently inhibit HIV reverse transcription.

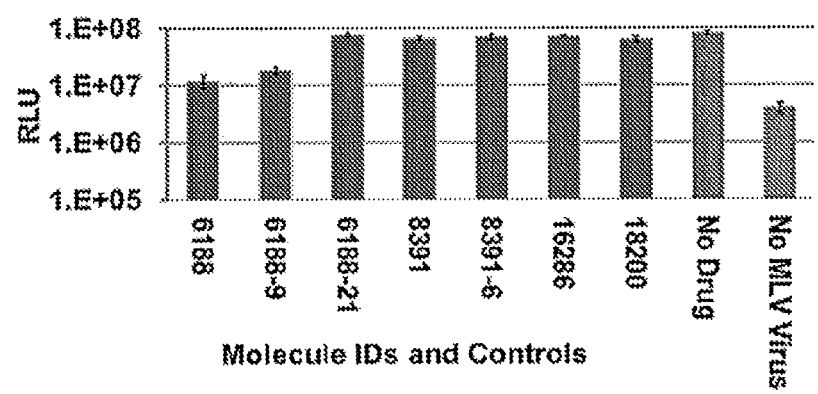
Fig. 16: Specificity Assay: Little Effect of Hits on MLV Propagation in Cell Culture.

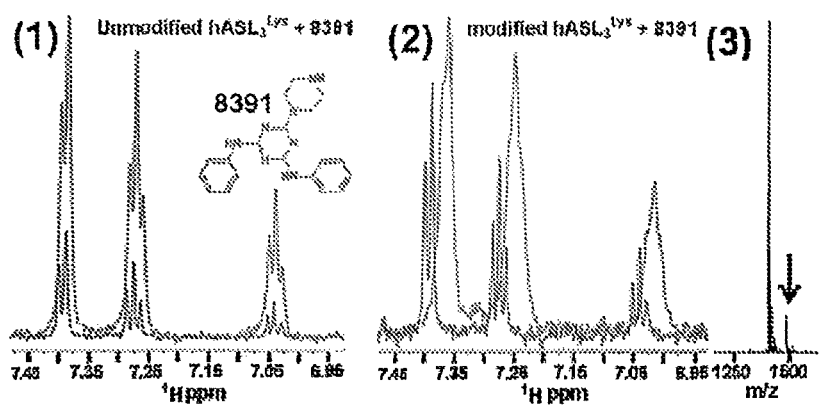
Fig. 17: Specificity Assay: Saturation Transfer Difference NMR Spectroscopy and MS spectra of 8391 small molecule when introduced to modified and unmodified htRNA$_3^{Lys}$.

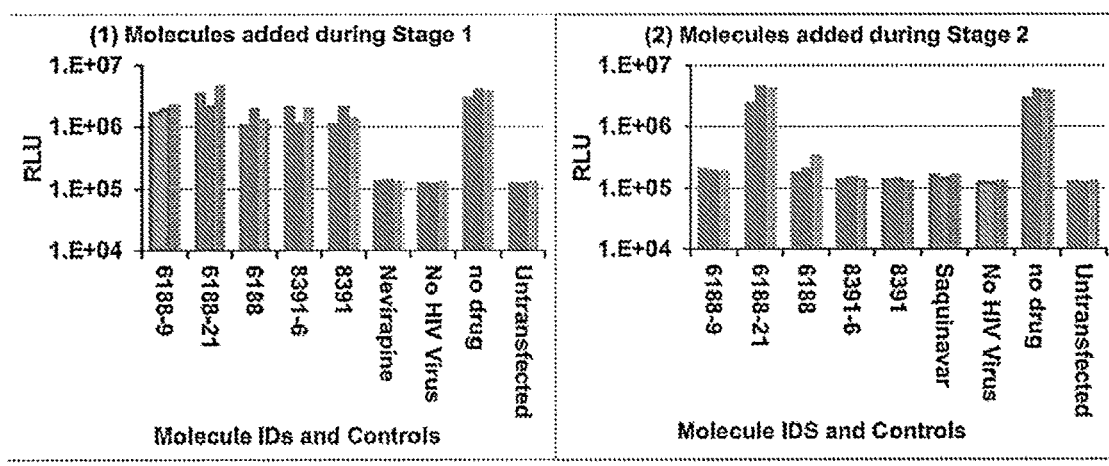
Fig. 18: Specificity Assay: Viral Propagation is affected by Hits during Stage 2 (Integration, Transcription, Translation and Assembly) and not during Stage 1 (Uncoating and Reverse Transcription ).

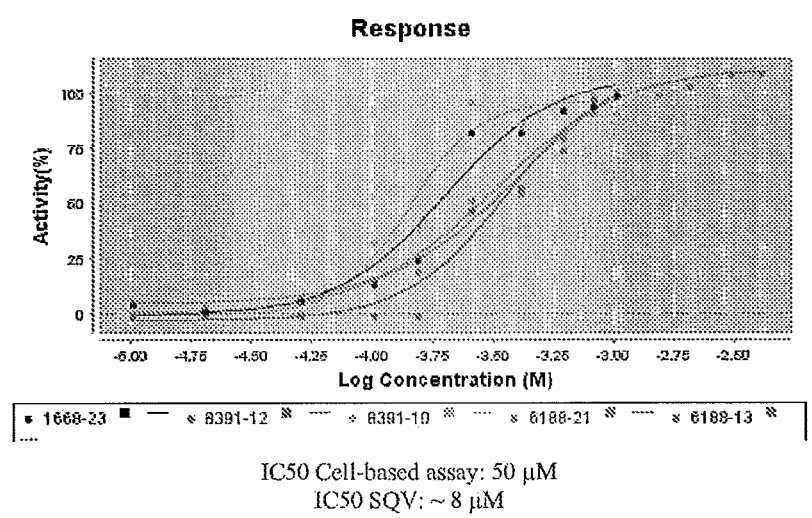
IC50 Cell-based assay: 50 μM
IC50 SQV: ~ 8 μM
Fig. 19: IC50 of Hit Compounds and Control

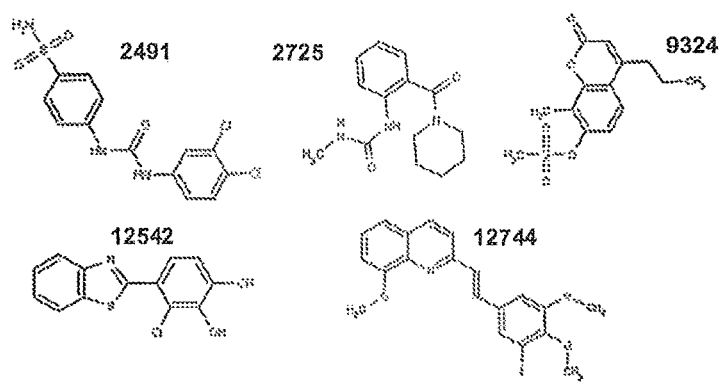
Fig. 20: Small molecule hits. Examples of compounds selected from Levels 1 and 2 Screens that inhibited HIV propagation in human cells (Figs. 10 and 11), and peptide interaction with modified hASL$_3^{Lys}$ (Fig. 12).

SMALL MOLECULE INHIBITORS OF VIRAL PROTEIN INTERACTIONS WITH HUMAN T-RNA

CROSS-REFERENCE TO RELATED APPLICATIONS

This application claims the benefit of U.S. Provisional Application Ser. No. 61/680,064, filed Aug. 6, 2012, which is herein incorporated by reference in its entirety for all purposes.

BACKGROUND

There are about 1.6 million people living with HIV/AIDS in North America while 33 million people suffer from the same disease worldwide. The HIV/AIDS epidemic is driven by a rapidly replicating retrovirus that undergoes multiple mutations to current therapeutics and as such, it is extremely challenging to treat successfully. For millions of patients whose viral strain is resistant to available HIV therapies, the consequences can be fatal. One option currently available for these patients is to use a combination of medications that leads to various side effects. Although progress has been made in the global fight against HIV/AIDS, the epidemic continues to devastate the US with 56,300 new HIV infections each year and the international community with even more. There is an unmet need to discover and develop new HIV therapeutics that can successfully counter the HIV's drug resistances. New validated targets and novel therapeutics need to be identified and developed for this purpose. (Cohen, J. *Science*, 2010, 330, 1301).

An intensive effort over the past twenty years has led to the development of several classes of effective antiviral drugs that have significantly improved patient survival (Simon et al., *Lancet*, 2006, 368, 489-584). However, current drug regimens control, but not eradicate HIV-1 in the infected patient, necessitating a long-term treatment. This unavoidably leads to problems of drug tolerance and resistance limiting treatment options for many patients. The seriousness of drug resistance has driven researchers to identify novel drugs that target previously untested biochemical steps in the HIV-1 replication cycle (Adamson et al., Drug Discov. Today, 2008, 13, 424-432; Greene et al., *Antiviral Res.* 2008, 80, 251-265). Current invention is exploiting one such critical step in HIV replication for the design and development of new therapeutics.

All retroviruses use a particular host cell transfer RNA (tRNA) as the primer for reverse transcription (RT) of their single-stranded RNA genomes into double-stranded DNA. HIV is a lentivirus and as such, uses the human $tRNA_3^{Lys}$ ($htRNA_3^{Lys}$, also known as $tRNA^{Lys3}$ or $tRNA^{Lys3}{}_{UUU}$ where the UUU is the tRNA's anticodon or $tRNA^{Lys3}{}_{SUU}$ where the S refers to the natural modified nucleoside in the anticodon, 5-methoxycarbonylmethyl-2-thiouridine) species as the primer of RT (Marquet et al., *Biochimie*. 1995, 77, 113-124; Arts et al., *PNAS* 1996, 93, 10063-10068; Kleiman et al., *FEBS Lett.* 2010, 584, 359-365.). Mutations at the primer binding site (PBS) are not sufficient to produce a lasting substitution of another human tRNA as the primer (Moore-Rigdon, K. et al., *Retrovirology* 2005, 2, 21). Prolonged culturing of the mutants results in reversion to $htRNA_3^{Lys}$ as the primer for RT (Id.).

The majority of clinically approved drugs target the viral enzymes reverse transcriptase (RT) and protease (PR). RT inhibitors fall into one of two classes based on their mode of action: the nucleoside-analog RT inhibitors (NRTIs) are incorporated into the growing DNA strand and serve as chain terminators; and the non-nucleoside RT inhibitors (NNRTIs) bind RT and induce conformational changes that inhibit RT polymerization activity (Jochmans, D. *Virus Res.* 2008, 134, 171-185). A better understanding of the viral life cycle and biochemistry has led to viral protease inhibitors (PIs) (Schultz et al., *Virus Res.* 2008, 134, 86-103). PIs competitively inhibit PR enzymatic function by binding to the active site of the enzyme (Mitsuya et al., *Adv. Pharmacol.* 2008, 56, 169-197) preventing proteolytic cleavage events associated with particle maturation. The result is the formation of non-infectious, immature virus particles.

Unfortunately, there are hundreds of mutations of HIV that result in resistance to these drugs. For some, such as the NRTIs like lamivudine, and all available non-nucleoside reverse transcriptase inhibitors (NNRTIs), a single mutation induces high-grade resistance, and for the most part does so in a predictable manner. For others such as zidovudine, abacavir, tenofovir, and most of the protease inhibitors (PIs), high-grade resistance requires the serial accumulation of multiple mutations and is slower to emerge. Others, including didanosine and stavudine also produce low levels of drug resistance in some cases (Adamson et al., *Mol. Interv.* 2009, 9, 70-74). Thus, the field of HIV research must remain actively engaged in developing new drugs against novel targets.

BRIEF DESCRIPTION OF THE DRAWINGS

FIG. 1: Schematics of the HIV life cycle.

FIG. 2: Schematics of interaction of HIV proteins with $htRNA_3^{Lys}$.

FIG. 3: Schematics of fluorescein conjugated peptide and fluorescence increase when small molecule competes with its binding to $hASL_3^{Lys}$.

FIG. 4: Sequence and secondary structure of $hASL_3^{Lys}$, and modified chemical structures and $hASL_3^{Lys}$ bound by HIV NCp7 and by a phage library selected peptide in a modification-dependent manner.

FIG. 5: Fluorescence quenching of NCp7's one tryptophan through binding of $hASL_3^{Lys}$-$mcm^5s^2U_{34}$; $ms^2t^6A_{37}$ or unmodified $ASL^{Lys}$.

FIG. 6: Fluorescence quenching of FITC conjugated peptide #6 (P6) through binding of $hASL_3^{Lys}$-$mcm^5s^2U_{34}$; $ms^2t^6A_{37}$ or unmodified $ASL_3^{Lys}$.

FIG. 7: Circular Dichroism (CD) spectra of NCp7 and P6 complexes with $hASL_3^{Lys}$-$mcm^5s^2U_{34}$; $ms^2t^6A_{37}$.

FIG. 8: Molecular Dynamics Simulation (MDS) Docking experiment (in silico) between $hASL_3^{Lys}$ and small molecules. Small molecules are screened for their high affinity (lowest free energy structure of the complex) and their binding to that part of the anticodon domain that makes it unique, the naturally occurring modifications.

FIG. 9: Schematic of HIV life cycle when small molecule competes with binding to $htRNA_3^{Lys}$.

FIG. 10: Level 1 screen with HIV cell based assay of the 1000 selected small molecules screened at their highest non-toxic concentrations.

FIG. 11: Level 2 screen using HIV cell based assay of the selected small molecules screened in a concentration dependent manner.

FIG. 13: Effect of small molecules on NL43, HXB and JRC-SF strains of HIV.

FIG. 14: Effect of small molecules on cell culture HIV viral propagation compared to commercial drugs Saquinavir and Nevirapine with a standard and tri-therapy resistant HIV strains.

FIG. 15: Specificity of various identified bioactive small molecules.

FIG. 16: Specificity assay which demonstrates that various small molecule hits have little to no effect on MLV propagation in cell culture.

FIG. 17. Saturation Transfer Difference (STD)-Nuclear Magnetic Resonance (NMR) of bioactive molecule 8391 with unmodified hASL$_3^{Lys}$ (1) and modified hASL$_3^{Lys}$ (2); (3) MS of the complex modified hASL$_3^{Lys}$-8391. For each set of NMR experiments, there is a one-dimensional NMR reference spectrum (Red) and a STD spectrum (Cyan). The spectral region 7.45-6.45 ppm displayed the chemical shifts of the aromatic protons of 8391 (highlighted in red on the structure). The STD-NMR and Mass Spectrometry (MS) spectra confirmed the complex modified hASL$_3^{Lys}$-8391 formation and that modified nucleotides are required for specific recognition of hASL$_3^{Lys}$-8391 and stronger affinity. The arrow (3) denotes MS peak of the complex modified hASL$_3^{Lys}$-8391.

FIG. 18: Specificity assay which demonstrates that HIV viral propagation is affected by hits during viral Assembly and not during Integration, Transcription, and Translation that occur during the HIV life cycle.

FIG. 19: IC50 of small molecule hits and control.

FIG. 20: Various small molecule hits selected from Level 1 Screen and Level 2 Screens.

SUMMARY OF THE INVENTION

Figure 12A:
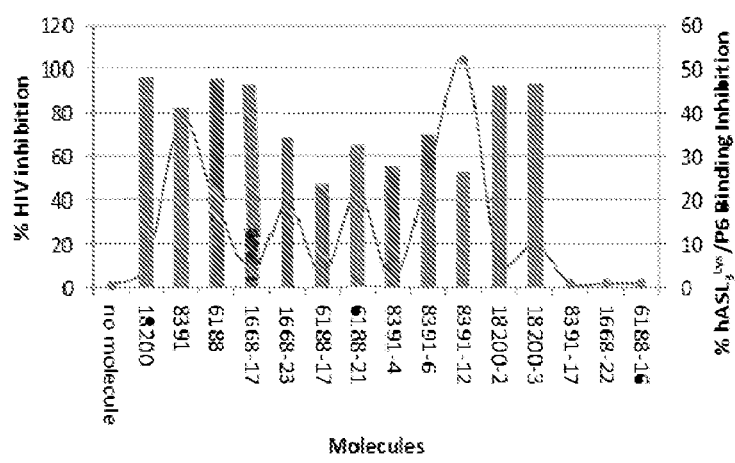
FIGS. 12 A, B, and C: Small molecules screened using Mechanism Based Secondary (MBS) and HIV cell based assays. The Mechanism Based Secondary Assay may be conducted in vitro and is a competition for binding to the anticodon domain by the small compound and the fluorescent reporter peptide that mimics HIV proteins, such as the nucleocapsid protein and possible human proteins recruited by the HIV infection, in binding the tRNA.

The present invention provides new HIV therapeutic compounds, compositions and methods of their use, wherein such compositions are less prone to develop HIV drug resistance.

Unlike the mechanisms of action of all other drugs approved or in clinical trials to treat HIV, the present invention's target of a tRNA/protein interaction: (1) does not occur in non-infected cells; (2) is critical to viral replication; (3) would be extremely difficult for the virus to develop resistance; and (4) to our knowledge is not being exploited by others.

This summary is merely exemplary of the numerous and varied embodiments described herein. The present invention is directed to compounds, compositions and methods of treating HIV/AIDS disease by administering an effective amount of a small molecule compound that inhibits viral preparation or viral recruitment of human tRNA. In one aspect of the invention, the human tRNA is htRNA$_3^{Lys}$.

One aspect of the present invention includes methods of using small molecule inhibitors to inhibit or disrupt viral preparation or viral recruitment of human tRNA. In one aspect of the invention, the human tRNA is htRNA$_3^{Lys}$.

Another aspect of the invention is a method of using small molecule inhibitors to inhibit interaction of viral proteins with human tRNA. In one aspect of the invention, the human tRNA is htRNA$_3^{Lys}$.

DETAILED DESCRIPTION OF THE INVENTION

All publications, patents and patent applications, including any drawings and appendices herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed inventions, or that any publication specifically or implicitly referenced is prior art.

In the Summary of the Invention above and in the Detailed Description of the invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

It is to be understood that the terminology used herein is for the purpose of describing particular embodiments only and is not intended to be limiting. Throughout the specification and claims, a given chemical formula or name shall encompass all optical isomers, racemic mixtures, analogs, solvates, hydrates, polymorphs, geometrical isomers, tautomers, pharmaceutically acceptable salts, and prodrugs thereof. The compounds disclosed herein can be administered by themselves, with pharmaceutically accepted excipients known in the skill of art, or in combination with other pharmaceutically active agents. The compounds can also be administered sequentially with other pharmaceutically active agents. Sequentially means immediately after or after 5, 10, 15, 20, 25, 30, 35, 40, 45, 50, 55, or 60 mins, or in some instances, between 1 min and 24 hours.

Unless defined otherwise, all technical and scientific terms used herein have the same meaning as commonly understood to one of the ordinary skill in the art to which the presently disclosed matter belongs. Although any methods and materials similar or equivalents to those described herein can be used in the practice or testing of the presently disclosed subject matter, representative methods and materials are herein described.

The term "about" as used herein when referring to a measurable value such as the amount of weight, time, dose, etc. is meant to encompass in one example variations of ±20% or ±15% or ±10% or in another example ±5%, in another example ±1%, or in some examples, ±0.1% of the specified amount, as such variations are appropriate to perform the disclosed methods.

The term "comprises" and grammatical equivalents thereof are used herein to mean that other components, ingredients, steps, etc. are optionally present. For example, an article "comprising" (or "which comprises") components A, B, and C can contain components A, B, and C or can contain not only A. B, and C, but also one or more other components.

As used herein, the term "alkyl" refers to C1-C20 inclusive, linear (i.e. straight chain), branched, cyclic (a "cycloalkyl"), saturated or at least partially and in some cases fully saturated (i.e. alkenyl or alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, methylpropynyl, butynyl, pentynyl, hexynyl, heptynyl and alkenyl groups. "Branched" refers to an alkyl group in which a lower alkyl group, such as methyl, ethyl, propyl or butyl is attached to a linear alkyl chain. "lower alkyl" refers to an alkyl group having 1 to about 8 carbon atoms (i.e., a C1-C8 alkyl). e.g., 1, 2, 3, 4, 5, 6, 7, or 8 carbon atoms. "Higher alkyl" refers to alkyl group having about 10 to about 20 carbon atoms, e.g., 10, 11, 12, 13, 14, 15, 16, 17, 18, 19 and 20 carbon atoms. In some embodiments of the invention, the alkyl groups are "C1 to C6 alkyl" such as methyl, ethyl, propyl, isopropyl, n-butyl, iso-butyl, sec-butyl, tert-butyl, amyl, tert-amyl, hexyl and the like. Some of the preferred alkyl groups of the invention have 2 or more carbon atoms.

In some embodiments of the invention, the alkyl groups are substituted. "Substituted alkyl" denote that the alkyl groups are substituted with one or more substitutents, preferably, halogen, hydroxy, carboxyl, S-alkyl, alkoxy, aryl, heteroaryl, heterocyclyl, amino, carbomyl, carbonyl, carboxamide, cyano, sulfonyl, methyl, ethyl, propyl, isopropyl, butyl, isobutyl, tert-butyl, trifluoromethyl, trifluoromethoxy and the like.

"Alkylether" means generally or alkyl-O-alkyl, with alkyl groups as defined above.

"Alkoxy" refers to an OR group wherein R is an alkyl or substituted alkyl.

Cycloalkyl residues are hydrocarbon groups within a molecule that comprise at least one ring having 3 to 8 carbon atoms linked into a ring. Examples of such cycloalkyl residues include cyclopropyl, cyclobutyl, cyclopentyl, cyclohexyl, cycloheptyl, cyclooctyl rings, and saturated bicyclic or fused polycyclic cycloalkanes such as decalin groups, and the like. "Substituted cycloalkyl" means above cycloalkyl rings are substituted preferably with one or more substitutents, such as alkyl, aryl, heteroaryl, cycloalkyl, halogen, hydroxy, carboxyl, carbonyl, S-alkyl, alkoxy, aryl, heteroaryl, heterocyclyl, amino, carbomyl, carboxamide, cyano, sulfonyl, methyl, ethyl, propyl, isopropyl, butyl, isobutyl, tert-butyl, trifluoromethyl, trifluoromethoxy and the like.

The term "heterocycle" or "heterocyclic ring" denotes optionally substituted 3 to 8 membered ring having one or more carbon atoms connected in the ring that also have 1 to 5 heteroatoms, such as oxygen, sulfur and/or nitrogen inserted into the ring. The 3 to 8 membered rings may be saturated, unsaturated or partially saturated, but are preferably saturated. The 3 to 8 membered rings can also be substituted with one or more substituents. Examples of a heterocycle group include, but are not limited to, aziridine, oxirane, thiarane, azetidine, oxetane, thietane, pyrrolidine, tetrahydrofuran, pyran, thiopyran, thiomorpholine, thiomorpholine S-oxide, thiomorpholine S-dioxide, oxazoline, tetrahydrothiophene, piperidine, tetrahydropyran, thiane, imidazolidine, oxazolidine, thiazolidine, dioxolane, dithiolane, piperazine, oxazine, dithiane, and dioxane.

An "aryl" group refers to a monocyclic aromatic, linked bicyclic aromatic or fused bicyclic aromatic moiety comprising at least one 6 membered aromatic "benzene" ring, preferably comprising 6 to 14 carbon atoms, such as phenyl, napthyl, anthracene, tetralin, indene, and indane. In some embodiments, the aryl groups are substituted with one or more substitutents.

The term "heteroaryl" means a heterocyclic aryl derivative which preferably contains a five-membered or six-membered conjugated and aromatic ring system having from 1 to 4 heteroatoms, such as oxygen, sulfur and/or nitrogen inserted into the unsaturated and conjugated heterocyclic ring. Heteroaryl groups include monocyclic heteroaromatic, linked bicyclic heteroaromatic or fused bicyclic heteroaromatic, or fused bicyclic heteroaromatic moieties. Examples of heteroaryls include pyridinyl, pyrimidinyl, pyrazinyl, pyridazinyl, pyrrolyl, furanyl, thiofuranyl, oxazolyl, isooxazolyl, phthalimido, thiazolyl, quinolyl, isoquinolinyl, indolyl, or a furan or thiofuran directly bonded to a phenyl, pyridyl, or pyrrolyl ring and like unsaturated and conjugated heteroaromatic rings. Any monocyclic, linked bicyclic, or fused bicyclic heteroaryl ring system which has the characteristics of aromaticity in terms of electron distribution throughout the ring system is included in this definition. Typically, the heteroaromatic ring systems contain 3 to 12 ring carbon atoms and 1 to 5 ring heteroatoms independently selected from oxygen, nitrogen, and sulfur atoms. In some embodiments of the invention, the heteroaryl groups are substituted with one or more substitutents.

The terms "arylalkyl" and heteroarylalkyl" refer to aromatic and heteroaromatic systems which are coupled to another residue through a carbon chain, including substituted or unsubstituted, saturated or unsaturated carbon chains, typically of 1 to 6 carbons. These carbon chains may include a carbonyl group, thus making them able to provide substitutents as an acyl moiety. Preferably, arylalkyl or heteroarylalkyl is an alkyl group substituted at any position by an aryl group, substituted aryl, heteroaryl or substituted heteroaryl. Preferred groups include benzyl, 2-phenyl ethyl, 3-phenylpropyl, 4-phenyl-n-butyl, 3-phenyl-n-amyl, 3-phenyl-2-butyl, 2-pyridinylmethyl, 2(2-pyridinyl)ethyl, and the like. Likewise, arylakyl or heteroarylalkyl may also include groups such as Ar—R—Ar or heteroAr—R—Ar or heteroAr—R-heteroAr, and the like.

By the term "effective amount" of a compound as provided herein is meant a sufficient amount of a compound to provide the desired regulation of a desired function, such as gene expression, protein function, inhibition of an enzyme, agonism or antagonism of a receptor, or a disease condition. As will be known in the skill of art, the exact amount required will vary from subject to subject, depending on the species, age, general condition of the subject, the use of complementary therapeutics, specific identity and formulation of the drug. Thus it is not possible to specify an exact "effective amount." However, an appropriate effective amount can be determined by one of ordinary skill in the art using only routine experimentation.

It must be noted that, as used in the specification and the appended claims, the singular forms, "a", "an" and "the" include plural referents unless the context clearly dictates otherwise. Thus, for example, reference to "an aromatic compound" includes mixtures of aromatic compounds.

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl groups may or may not be substituted and that the description includes both the unsubstituted lower alkyl and substituted lower alkyl.

The term "salts" means pharmaceutically acceptable salts commonly used to form alkali metal salts of free acids and to form addition salts of free bases. The nature of the salt is not critical, provided that it is pharmaceutically-acceptable. Suitable pharmaceutically-acceptable acid addition salts include, for example, those prepared from an inorganic acid or from an organic acid. Nonlimiting examples of such inorganic acids are hydrochloric, hydrobromic, hydroiodic, nitric, carbonic, sulfuric and phosphoric acid. Appropriate organic acids include, without limitation, aliphatic, cycloaliphatic, aromatic, arylaliphatic, and heterocyclyl containing carboxylic acids or sulfonic acids. Nonlimiting examples of organic acids are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid. Suitable pharmaceutically-acceptable salts of free acid-containing compounds disclosed herein include metallic salts and organic salts. Examples of metallic salts include, but are not limited to, appropriate alkali metal (group Ia) salts, alkaline earth metal (group IIa) salts and other physiological acceptable metals. In some embodiments, such salts are made from aluminum, calcium, lithium, magnesium, potassium, sodium and zinc. In some embodiments, organic salts are made from primary amines, secondary amines, tertiary amines and quaternary ammonium salts, including in part, tromethamine, diethylamine, tetra-N-methylammonium, N,N'-dibenzylethylenediamine, chloroprocaine, choline, diethanolamine, ethylenediamine, meglumine (N-methylglucamine) and procaine.

The terms "administer", "administering", or "administration" as used in this disclosure refer to either directly administering a compound or pharmaceutically acceptable salt of the compound or a composition to a subject, or administering a prodrug derivative or analog of the compound or pharmaceutically acceptable salt of the compound or composition to the subject, which forms an equivalent amount of active compound within the subject's body.

ChemDraw version 8.0 or 10 (CambridgeSoft Corporation, Cambridge, Mass.) was used to name structures.

One aspect of the invention provides compounds, compositions and methods of treating HIV disease by inhibiting interaction of viral proteins with human tRNA in a subject in need thereof, comprising administration of a therapeutically effective amount of a compound, that has a preferential specificity and/or binding affinity to human $tRNA_3^{Lys}$.

Another aspect of the invention provides methods of treating HIV disease by inhibiting interaction of viral proteins with human tRNA in a subject in need thereof, comprising administration of a therapeutically effective amount of a compound, that has a preferential specificity and/or binding affinity to human $tRNA_3^{Lys}$, wherein the compound is selected from the group consisting of compounds of formula (I), (II), (III), (IV), (V), (VI), (VII), (VIII), or (IX).

The present invention also includes compounds, compositions and methods of administering compositions to prevent, inhibit and/or treat HIV infection.

One aspect of the invention provides compounds of formula (I), compositions comprising compounds of formula (I), or methods of treatment of HIV disease in a patient in need thereof, comprising administration of a therapeutically effective amount of compound of formula (I) to a subject in need thereof:

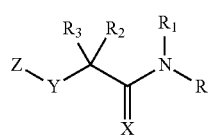

(I)

wherein;

X is O or S;

Y is O, $CH_2$, or $CR_4R_5$ wherein $R_4$ and $R_5$ are independently and individually H, heteroalkyl, substituted or unsubstituted aryl, substituted or unsubstituted heteroaryl, substituted or unsubstituted aralkyl, substituted or unsubstituted C1-C4 alkyl, branched C3-C7 alkyl, or substituted or unsubstituted C3-C7 cycloalkyl;

R1 and R are independently and individually H, heteroalkyl, 3-8 membered heterocycle, substituted or unsubstituted aryl, substituted or unsubstituted heteroaryl, substituted or unsubstituted aralkyl, substituted or unsubstituted C1-C4 alkyl, branched C3-C7 alkyl, or substituted or unsubstituted C3-C7 cycloalkyl wherein in each instance, or optionally R1 and R connected together to form a ring;

wherein the ring is substituted with one or more alkyl, aryl, heteroaryl, aralkyl, or heteroatoms;

$R_2$ and $R_3$ are independently and individually H, heteroalkyl, 3-8 membered heterocycle, substituted or unsubstituted aryl, substituted or unsubstituted heteroaryl, substituted or unsubstituted aralkyl, substituted or unsubstituted C1-C4 alkyl, branched C3-C7 alkyl, or substituted or unsubstituted C3-C7 cycloalkyl;

Z is substituted or unsubstituted C1-C4 alkyl, branched C3-C7 alkyl, substituted or unsubstituted C3-C7 cycloalkyl, substituted or unsubstituted aryl, substituted or unsubstituted heteroaryl, substituted or unsubstituted aralkyl;

and pharmaceutically acceptable salts, solvates, prodrugs, polymorphs, stereoisomers, and tautomers thereof.

One aspect of the invention provides methods of inhibiting viral recruitment and/or viral preparation of human $tRNA_3^{Lys}$ comprising use of a compound of formula (I):

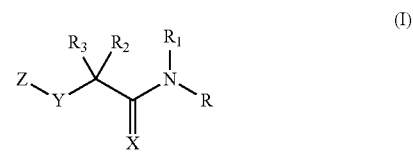

(I)

wherein;

X is O or S;

Y is O, $CH_2$, or $CR_4R_5$ wherein $R_4$ and $R_5$ are independently and individually H, heteroalkyl, substituted or unsubstituted aryl, substituted or unsubstituted heteroaryl, substituted or unsubstituted aralkyl, substituted or unsubstituted C1-C4 alkyl, branched C3-C7 alkyl, or substituted or unsubstituted C3-C7 cycloalkyl;

R1 and R are independently and individually H, heteroalkyl, 3-8 membered heterocycle, substituted or unsubstituted aryl, substituted or unsubstituted heteroaryl, substituted or unsubstituted aralkyl, substituted or unsubstituted C1-C4 alkyl, branched C3-C7 alkyl, or substituted or unsubstituted C3-C7 cycloalkyl wherein in each instance, or optionally R1 and R connected together to form a ring; wherein the ring is substituted with one or more alkyl, aryl, heteroaryl, aralkyl, or heteroatoms;

$R_2$ and $R_3$ are independently and individually H, heteroalkyl, 3-8 membered heterocycle, substituted or unsubstituted aryl, substituted or unsubstituted heteroaryl, substituted or unsubstituted aralkyl, substituted or unsubstituted C1-C4 alkyl, branched C3-C7 alkyl, or substituted or unsubstituted C3-C7 cycloalkyl;

Z is substituted or unsubstituted C1-C4 alkyl, branched C3-C7 alkyl, substituted or unsubstituted C3-C7 cycloalkyl, substituted or unsubstituted aryl, substituted or unsubstituted heteroaryl, substituted or unsubstituted aralkyl;

and pharmaceutically acceptable salts, solvates, prodrugs, polymorphs, stereoisomers, and tautomers thereof.

One aspect of the invention provides compounds of formula (II), compositions comprising compounds of formula (I), or methods of treatment of HIV disease in a patient in need thereof, comprising administration of a therapeutically effective amount of compound of formula (II) to a subject in need thereof:

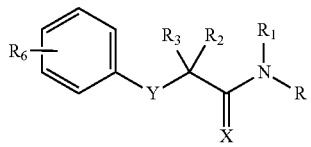

(II)

wherein;

X is O or S;

Y is O, $CH_2$, or $CR_4R_5$ wherein $R_4$ and $R_5$ are independently and individually H, heteroalkyl, substituted or unsubstituted aryl, substituted or unsubstituted heteroaryl, substituted or unsubstituted aralkyl, substituted or unsubstituted C1-C4 alkyl, branched C3-C7 alkyl, or substituted or unsubstituted C3-C7 cycloalkyl;

R1 and R are independently and individually H, heteroalkyl, 3-8 membered heterocycle, substituted or unsubstituted aryl, substituted or unsubstituted heteroaryl, substituted or unsubstituted aralkyl, substituted or unsubstituted C1-C4 alkyl, branched C3-C7 alkyl, or substituted or unsubstituted C3-C7 cycloalkyl wherein in each instance, or optionally R1 and R connected together to form a ring; wherein the ring is substituted with one or more alkyl, aryl, heteroaryl, aralkyl, or heteroatoms;

$R_2$ and $R_3$ are independently and individually H, heteroalkyl, 3-8 membered heterocycle, substituted or unsubstituted aryl, substituted or unsubstituted heteroaryl, substituted or unsubstituted aralkyl, substituted or unsubstituted C1-C4 alkyl, branched C3-C7 alkyl, or substituted or unsubstituted C3-C7 cycloalkyl;

$R_6$ is independently and individually selected from the group consisting of halo, hydroxyl, linear or branched C1-C4 alkyl, haloalkyl, hydroxyalkyl, alkoxy and alkoxyalkyl;

and pharmaceutically acceptable salts, solvates, prodrugs, polymorphs, stereoisomers, and tautomers thereof.

In another embodiment, the invention provides methods of inhibiting viral recruitment and/or viral preparation of human $tRNA_3^{Lys}$ comprising use of a compound of formula (II):

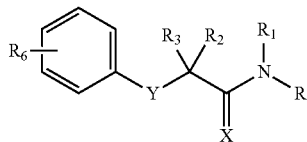

(II)

wherein;

X is O or S;

Y is O, $CH_2$, or $CR_4R_5$ wherein $R_4$ and $R_5$ are independently and individually H, heteroalkyl, substituted or unsubstituted aryl, substituted or unsubstituted heteroaryl, substituted or unsubstituted aralkyl, substituted or unsubstituted C1-C4 alkyl, branched C3-C7 alkyl, or substituted or unsubstituted C3-C7 cycloalkyl;

R1 and R are independently and individually H, heteroalkyl, 3-8 membered heterocycle, substituted or unsubstituted aryl, substituted or unsubstituted heteroaryl, substituted or unsubstituted aralkyl, substituted or unsubstituted C1-C4 alkyl, branched C3-C7 alkyl, or substituted or unsubstituted C3-C7 cycloalkyl wherein in each instance, or optionally R1 and R connected together to form a ring; wherein the ring is substituted with one or more alkyl, aryl, heteroaryl, aralkyl, or heteroatoms;

$R_2$ and $R_3$ are independently and individually H, heteroalkyl, 3-8 membered heterocycle, substituted or unsubstituted aryl, substituted or unsubstituted heteroaryl, substituted or unsubstituted aralkyl, substituted or unsubstituted C1-C4 alkyl, branched C3-C7 alkyl, or substituted or unsubstituted C3-C7 cycloalkyl;

$R_6$ is independently and individually selected from the group consisting of halo, hydroxyl, linear or branched C1-C4 alkyl, haloalkyl, hydroxyalkyl, alkoxy and alkoxyalkyl;

and pharmaceutically acceptable salts, solvates, prodrugs, polymorphs, stereoisomers, and tautomers thereof.

In one aspect, the present invention provides compounds of formula (III), compositions comprising compounds of formula (III), or methods of treatment of HIV disease in a patient in need thereof, comprising administration of a therapeutically effective amount of compound of formula (III) to a subject in need thereof:

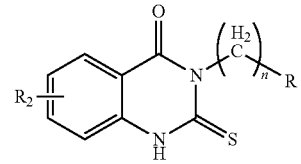

(III)

wherein;

n is 1, 2, 3, or 4 optionally n is $CH_2$—Y—Z, wherein Y is a carbocycle, heterocycle, aryl, or heteroaryl and Z is —$CONR_3R_4$, —$COOR_5$, —$OCOR_6$, —$NR_7COR_8$ or —$OR_9$, wherein each $R_3$, $R_4$, $R_5$, $R_6$, $R_7$, $R_8$ and $R_9$ is independently and individually H, heteroalkyl, aryl, heteroaryl, aralkyl, alkylaryl, alkylheteroaryl, C1-C4 alkyl, branched C3-C7 alkyl, or C3-C7 cycloalkyl;

R is independently and individually H, heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkene, —$NR_{10}R_{11}$, —$OR_{12}$, or $SR_3$, wherein each $R_{10}$, $R_{11}$, $R_{12}$ and $R_{13}$ is independently and individually heteroalkyl, aryl, heteroaryl, aralkyl, alkylaryl, alkylheteroaryl, C1-C4 alkyl, branched C3-C7 alkyl, or C3-C7 cycloalkyl;

$R_2$ is independently an individually H, —COOR$_{14}$, —CONR$_{15}$R$_{16}$, —OR$_{17}$, —NR$_{19}$COR$_{20}$, or —OCOR$_{21}$ wherein each R$_{14}$, R$_{15}$, R$_{16}$, R$_{17}$, R$_{19}$, R$_{20}$ and R$_{21}$ is independently an individually H, C1-C4 alkyl, —(CH$_2$)$_n$—X—R', —(CH$_2$)$_n$-carbocycle, —(CH$_2$)$_n$-heterocycle, —(CH$_2$)$_n$-aryl, and —(CH$_2$)$_n$-heteroaryl, wherein R' is alkyl, aryl or heteroaryl, n is 1, 2, 3, or 4, and X is O, S, or N, and optionally R$_{15}$ and R$_{16}$ connected together to form a ring; and pharmaceutically acceptable salts, solvates, prodrugs, polymorphs, stereoisomers, and tautomers thereof.

Another aspect of the invention provides methods of inhibiting viral recruitment and/or viral preparation of human tRNA$_3^{Lys}$ comprising use of a compound of formula (III):

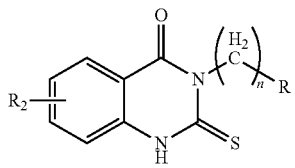

(III)

n is 1, 2, 3, or 4 optionally n is CH$_2$—Y—Z, wherein Y is a carbocycle, heterocycle, aryl, or heteroaryl and Z is —CONR$_3$R$_4$, —COOR$_5$, —OCOR$_6$, —NR$_7$COR$_8$ or —OR$_9$, wherein each R$_3$, R$_4$, R$_5$, R$_6$, R$_7$, R$_8$ and R$_9$ is independently and individually H, heteroalkyl, aryl, heteroaryl, aralkyl, alkylaryl, alkylheteroaryl, C1-C4 alkyl, branched C3-C7 alkyl, or C3-C7 cycloalkyl;

R is independently and individually H, heteroalkyl, aryl, heteroaryl, aralkyl, alkylaryl, alkylheteroaryl, alkyle-ther, C1-C4 alkyl, branched C3-C7 alkyl, C3-C7 cycloalkyl, C3-C7 heterocycle, C3-C7 cycloalkene, —NR$_{10}$R$_{11}$, —OR$_{12}$, or SR$_{13}$, wherein each R$_{10}$, R$_{11}$, R$_{12}$ and R$_{13}$ is independently and individually heteroalkyl, aryl, heteroaryl, aralkyl, alkylaryl, alkylheteroaryl, C1-C4 alkyl, branched C3-C7 alkyl, or C3-C7 cycloalkyl;

$R_2$ is independently an individually H, —COOR$_{14}$, —CONR$_{15}$R$_{16}$, —OR$_{17}$, —NR$_{19}$COR$_{20}$, —OCOR$_{21}$ wherein each R$_{14}$, R$_{15}$, R$_{16}$, R$_{17}$, R$_{19}$, R$_{20}$ and R$_{21}$ is independently an individually H, C1-C4 alkyl, —(CH$_2$)$_n$—X—R', —(CH$_2$)$_n$-carbocycle, —(CH$_2$)$_n$-heterocycle, —(CH$_2$)$_n$-aryl, and —(CH$_2$)$_n$-heteroaryl, wherein R' is alkyl, aryl or heteroaryl, n is 1, 2, 3, or 4, and X is O, S, or N, and optionally R$_{15}$ and R$_{16}$ connected together to form a ring; and pharmaceutically acceptable salts, solvates, prodrugs, polymorphs, stereoisomers, and tautomers thereof.

One aspect of the present invention provides compounds of formula (IV), compositions comprising compounds of formula (IV), or methods of treatment of HIV disease in a patient in need thereof, comprising administration of a therapeutically effective amount of compound of formula (IV) to a subject in need thereof:

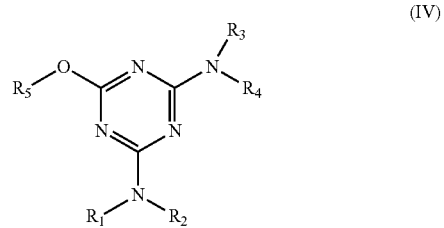

(IV)

wherein:
R$_1$ and R$_2$ are independently and individually H, heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane, —NH$_2$, or R$_1$ and R$_2$ connected together to form a 3-7 membered ring, and wherein the ring is a piperazine, piperidine, morpholine, thiomorpholine, thiazole or a pyrrolidine, each substituted or unsubstituted;

R$_3$ and R$_4$ are independently and individually H, heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane, or R$_3$ and R$_4$ connected together to form a 3-7 membered ring, and wherein the ring is a piperazine, piperidine, morpholine, thiomorpholine, thiazole or a pyrrolidine, each substituted or unsubstituted;

R$_5$ is independently and individually H, heteroalkyl, aryl, heteroaryl, aralkyl, alkylaryl, alkylheteroaryl, alkylether, C1-C4 alkyl, branched C3-C7 alkyl. C3-C7 cycloalkyl, C3-C7 heterocycle, C3-C7 cycloalkane, C1-C4 alkylfluoromethyl, C1-C4 alkyldifluoromethyl, or C1-C4 alkyltrifluoromethyl; and pharmaceutically acceptable salts, solvates, prodrugs, polymorphs, stereoisomers, and tautomers thereof.

In another embodiment, the invention provides methods of inhibiting viral recruitment and/or viral preparation of human tRNA$_3^{Lys}$ comprising use of a compound of formula (IV).

Another aspect of the present invention provides compounds of formula (V), compositions comprising compounds of formula (V), or methods of treatment of HIV disease in a patient in need thereof, comprising administration of a therapeutically effective amount of compound of formula (V) to a subject in need thereof:

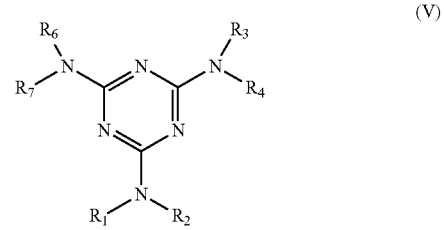

(V)

wherein:
R$_1$ and R$_2$ are independently and individually H, heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane, —NH$_2$, or R$_1$ and R$_2$ connected together to form a 3-7 membered ring, and wherein the ring is a piperazine, piperidine, morpholine, thiomorpholine, or a pyrrolidine, each substituted or unsubstituted;

$R_3$, $R_4$, $R_6$, and $R_7$ are independently and individually H, heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane, or $R_3$ and $R_4$ connected together to form a 3-7 membered ring, and wherein the ring is a piperazine, piperidine, morpholine, thiomorpholine, thiazole or a pyrrolidine, each substituted or unsubstituted or $R_6$ and $R_7$ connected together to form a 3-7 membered ring, and wherein the ring is a piperazine, piperidine, morpholine, thiomorpholine, or a pyrrolidine, each substituted or unsubstituted; and pharmaceutically acceptable salts, solvates, prodrugs, polymorphs, stereoisomers, and tautomers thereof.

One more aspect of the present invention provides methods of inhibiting viral recruitment and/or viral preparation of human tRNA$_3^{Lys}$ comprising use of a compound of formula (V):

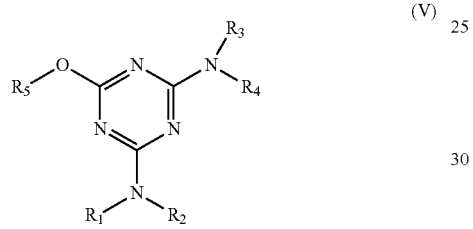

wherein:

$R_1$ and $R_2$ are independently and individually H, heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane, —NH$_2$, or $R_1$ and $R_2$ connected together to form a 3-7 membered ring, and wherein the ring is a piperazine, piperidine, morpholine, thiomorpholine, thiazole or a pyrrolidine, each substituted or unsubstituted:

$R_3$ and $R_4$ are independently and individually H, heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane, or $R_3$ and $R_4$ connected together to form a 3-7 membered ring, and wherein the ring is a piperazine, piperidine, morpholine, thiomorpholine, thiazole or a pyrrolidine, each substituted or unsubstituted;

$R_5$ is independently and individually H, heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane, C1-C4 alkylfluoromethyl, C1-C4 alkyldifluoromethyl, or C1-C4 alkyltrifluoromethyl; and pharmaceutically acceptable salts, solvates, prodrugs, polymorphs, stereoisomers, and tautomers thereof.

Another aspect of the present invention provides compounds of formula (VI), compositions comprising compounds of formula (VI), or methods of treatment of HIV disease in a patient in need thereof, comprising administration of a therapeutically effective amount of compound of formula (VI) to a subject in need thereof:

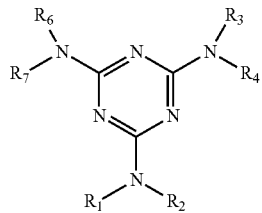

wherein:

$R_1$ and $R_2$ are independently and individually H, heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane, —NH$_2$, or $R_1$ and $R_2$ connected together to form a 3-7 membered ring, and wherein the ring is a piperazine, piperidine, morpholine, thiomorpholine, thiazole or a pyrrolidine, each substituted or unsubstituted;

$R_3$, $R_4$, $R_6$, and $R_7$ are independently and individually H, heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane, or $R_3$ and $R_4$ connected together to form a 3-7 membered ring, and wherein the ring is a piperazine, piperidine, morpholine, thiomorpholine, thiazole or a pyrrolidine, each substituted or unsubstituted or $R_6$ and $R_7$ connected together to form a 3-7 membered ring, and wherein the ring is a piperazine, piperidine, morpholine, thiomorpholine, thiazole or a pyrrolidine, each substituted or unsubstituted; and pharmaceutically acceptable salts, solvates, prodrugs, polymorphs, stereoisomers, and tautomers thereof.

One more aspect of the present invention provides methods of inhibiting viral recruitment and/or viral preparation of human tRNA$_3^{Lys}$ comprising use of a compound of formula (VI):

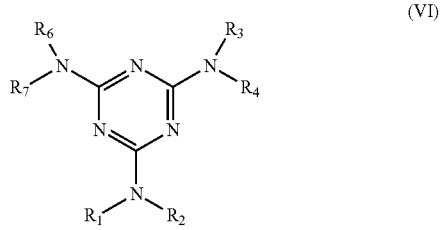

wherein:

$R_1$ and $R_2$ are independently and individually H, heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane, —NH$_2$, or $R_1$ and $R_2$ connected together to form a 3-7 membered ring, and wherein the ring is a piperazine, piperidine, morpholine, thiomorpholine, thiazole or a pyrrolidine, each substituted or unsubstituted;

$R_3$, $R_4$, $R_6$, and $R_7$ are independently and individually H, heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane, or $R_3$ and $R_4$ connected together to form a 3-7 membered ring, and wherein the ring is a piperazine, piperidine, morpholine, thiomorpholine, thiazole or a pyrrolidine, each substituted or unsubstituted or $R_6$ and $R_7$ connected together to form a 3-7 membered ring, and wherein the ring is a piperazine, piperidine, morpholine, thiomorpholine, thiazole or a pyrrolidine, each substituted or unsubstituted; and pharmaceutically acceptable salts, solvates, prodrugs, polymorphs, stereoisomers, and tautomers thereof.

One more aspect of the present invention provides compounds of formula (VII), compositions comprising compounds of formula (VII) or methods of treatment of HIV disease in a patient in need thereof, comprising administration of a therapeutically effective amount of compound of formula (VII) to a subject in need thereof:

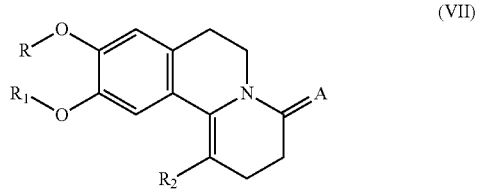

(VII)

wherein:

$R_2$ is —CN, —CO$_2$H, —COR', —COOR', —OR', —NHR', —SR', wherein R' is heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane;

R and $R_1$ is heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane;

A is O, N—X—R", wherein X is —C=O, —C=S, —C=NH, —SO$_2$—, R" is heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane; and pharmaceutically acceptable salts, solvates, prodrugs, polymorphs, stereoisomers, and tautomers thereof.

One aspect of the present invention provides methods of inhibiting viral recruitment and/or viral preparation of human tRNA$_3^{Lys}$ comprising use of a compound of formula (VII):

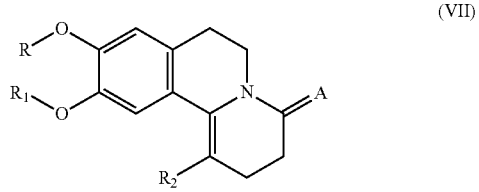

(VII)

wherein:

$R_2$ is —CN, —CO$_2$H, —COR', —COOR', —OR', —NHR', —SR', wherein R' is heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane;

R and $R_1$ is heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane;

A is O, N—X—R", wherein X is —C=O, —C=S, —C=NH, —SO$_2$—, R" is heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, C3-C7 cycloalkane; and pharmaceutically acceptable salts, solvates, prodrugs, polymorphs, stereoisomers, and tautomers thereof.

One more aspect of the present invention provides compounds of formula (VIII), compositions comprising compounds of formula (VIII), or methods of treatment of HIV disease in a patient in need thereof, comprising administration of a therapeutically effective amount of compound of formula (VIII) to a subject in need thereof:

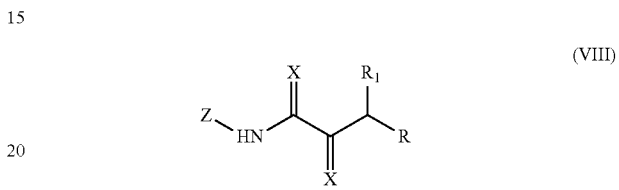

(VIII)

wherein;

X is O, S, —NH, or —SO$_2$—;

R1 and R are independently and individually H, heteroalkyl, 3-8 membered heterocycle, substituted or unsubstituted aryl, substituted or unsubstituted heteroaryl, substituted or unsubstituted aralkyl, substituted or unsubstituted C1-C4 alkyl, branched C3-C7 alkyl, substituted or unsubstituted C3-C7 cycloalkyl, or R1 and R are connected together to form a ring; wherein the ring is 3-8 membered substituted or unsubstituted heterocycle, substituted or unsubstituted aryl, substituted or unsubstituted heteroaryl, or substituted or unsubstituted C3-C7 cycloalkyl, and the ring is optionally substituted with one or more substituents independently selected from the group consisting of halo, hydroxyl, linear or branched C1-C4 alkyl, haloalkyl, hydroxyalkyl, alkoxy and alkoxyalkyl;

Z is substituted or unsubstituted C1-C4 alkyl, branched C3-C7 alkyl, substituted or unsubstituted C3-C7 cycloalkyl, substituted or unsubstituted aryl, substituted or unsubstituted heteroaryl, substituted or unsubstituted aralkyl; and pharmaceutically acceptable salts, solvates, prodrugs, polymorphs, stereoisomers, and tautomers thereof.

In a specific embodiment, Z is phenyl, optionally substituted with one or more substituents independently selected from the group consisting of halo, hydroxyl, linear or branched C1-C4 alkyl, haloalkyl, hydroxyalkyl, alkoxy and alkoxyalkyl.

One aspect of the present invention provides methods of inhibiting viral recruitment and/or viral preparation of human tRNA$_3^{Lys}$ comprising use of a compound of formula (VIII):

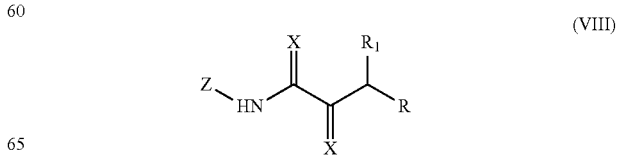

(VIII)

wherein;

X is O, S, —NH, or —SO$_2$—;

R1 and R are independently and individually H, heteroalkyl, 3-8 membered heterocycle, substituted or unsubstituted aryl, substituted or unsubstituted heteroaryl, substituted or unsubstituted aralkyl, substituted or unsubstituted C1-C4 alkyl, branched C3-C7 alkyl, substituted or unsubstituted C3-C7 cycloalkyl, or R1 and R are connected together to form a ring; wherein the ring is 3-8 membered substituted or unsubstituted heterocycle, substituted or unsubstituted aryl, substituted or unsubstituted heteroaryl, or substituted or unsubstituted C3-C7 cycloalkyl, and the ring is optionally substituted with one or more substituents independently selected from the group consisting of halo, hydroxyl, linear or branched C1-C4 alkyl, haloalkyl, hydroxyalkyl, alkoxy and alkoxyalkyl;

Z is substituted or unsubstituted C1-C4 alkyl, branched C3-C7 alkyl, substituted or unsubstituted C3-C7 cycloalkyl, substituted or unsubstituted aryl, substituted or unsubstituted heteroaryl, substituted or unsubstituted aralkyl; and pharmaceutically acceptable salts, solvates, prodrugs, polymorphs, stereoisomers, and tautomers thereof.

In a specific embodiment, Z is phenyl optionally substituted with one or more substituents independently selected from the group consisting of halo, hydroxyl, linear or branched C1-C4 alkyl, haloalkyl, hydroxyalkyl, alkoxy and alkoxyalkyl.

One more aspect of the present invention provides compounds of formula (VIII) and compositions comprising compounds of formula (VIII):

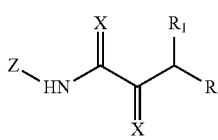

(VIII)

wherein;

X is O, S, —NH, or —SO$_2$—;

R1 and R are independently and individually H, heteroalkyl, 3-8 membered heterocycle, substituted or unsubstituted aryl, substituted or unsubstituted heteroaryl, substituted or unsubstituted aralkyl, substituted or unsubstituted C1-C4 alkyl, branched C3-C7 alkyl, substituted or unsubstituted C3-C7 cycloalkyl, or R1 and R are connected together to form a ring; wherein the ring is 3-8 membered substituted or unsubstituted heterocycle, substituted or unsubstituted aryl, substituted or unsubstituted heteroaryl, or substituted or unsubstituted C3-C7 cycloalkyl, and the ring is optionally substituted with one or more substituents independently selected from the group consisting of halo, hydroxyl, linear or branched C1-C4 alkyl, haloalkyl, hydroxyalkyl, alkoxy and alkoxyalkyl;

Z is substituted or unsubstituted C1-C4 alkyl, branched C3-C7 alkyl, substituted or unsubstituted C3-C7 cycloalkyl, substituted or unsubstituted aryl, substituted or unsubstituted heteroaryl, or substituted or unsubstituted aralkyl; and pharmaceutically acceptable salts thereof; with the proviso that formula (VIII) is not the following compound:

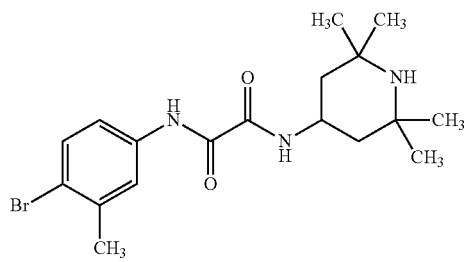 [SMILES: Cc1cc(NC(=O)C(=O)NC2CC(C)(C)NC(C)(C)C2)ccc1Br]

In another specific embodiment, the present invention provides compounds of formula (IX), compositions comprising compounds of formula (IX), or methods of treatment of HIV disease in a patient in need thereof, comprising administration of a therapeutically effective amount of compound of formula (IX) to a subject in need thereof:

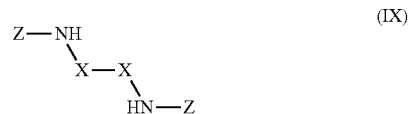

(IX)

wherein each instance of X is independently selected from the group consisting of: linear or branched $C_1$-$C_6$ alkyl, linear or branched $C_2$-$C_6$ alkenyl, or linear or branched $C_2$-$C_6$ alkynyl, wherein the linear or branched alkyl, alkenyl or alkynyls may include one or more spacer moieties selected from the group consisting of: O, S, NH(C=O), (C=O)NH, O(C=O), (C=O)O or (C=O);

Z is independently selected from the group consisting of: heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, and C3-C7 cycloalkane;

and pharmaceutically acceptable salts, solvates, prodrugs, polymorphs, stereoisomers, and tautomers thereof.

In a specific embodiment, Z is independently a ring from the group consisting of a piperazine, piperidine, morpholine, thiomorpholine, thiazole or a pyrrolidine, wherein each ring is optionally substituted with one or more substituents independently selected from the group consisting of halo, hydroxyl, linear or branched C1-C4 alkyl, haloalkyl, hydroxyalkyl, alkoxy and alkoxyalkyl.

One aspect of the present invention provides methods of inhibiting viral recruitment and/or viral preparation of human tRNA$_3^{Lys}$ comprising use of a compound of formula (IX):

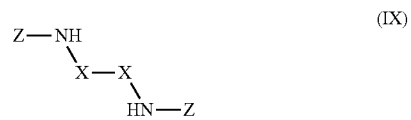

(IX)

wherein each instance of X is independently selected from the group consisting of: linear or branched $C_1$-$C_6$ alkyl, linear or branched $C_2$-$C_6$ alkenyl, or linear or branched $C_2$-$C_6$ alkynyl, wherein the linear or branched alkyl, alkenyl or alkynyls may include one or more spacer moieties selected from the group consisting of: O, S, NH(C=O), (C=O)NH, O(C=O), (C=O)O or (C=O);

Z is independently selected from the group consisting of: heteroalkyl, aryl, heteroaryl, aralkyl, alkylaryl, alkylheteroaryl, alkylether. C1-C4 alkyl, branched C3-C7 alkyl, C3-C7 cycloalkyl, C3-C7 heterocycle, and C3-C7 cycloalkane;

and pharmaceutically acceptable salts, solvates, prodrugs, polymorphs, stereoisomers, and tautomers thereof.

In a specific embodiment, Z is independently a ring selected from the group consisting of a piperazine, piperidine, morpholine, thiomorpholine, thiazole or a pyrrolidine, wherein each ring is optionally substituted with one or more substituents independently selected from the group consisting of halo, hydroxyl, linear or branched C1-C4 alkyl, haloalkyl, hydroxyalkyl, alkoxy and alkoxyalkyl.

In another specific embodiment, the present invention provides compounds of formula (IX) and compositions comprising compounds of formula (IX):

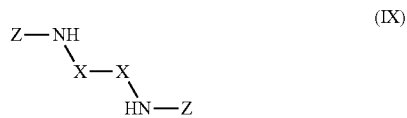
(IX)

wherein each instance of X is independently selected from the group consisting of: linear or branched $C_1$-$C_6$ alkyl, linear or branched $C_2$-$C_6$ alkenyl, or linear or branched $C_2$-$C_6$ alkynyl, wherein the linear or branched alkyl, alkenyl or alkynyls may include one or more spacer moieties selected from the group consisting of: O, S, NH(C=O), (C=O)NH, O(C=O), (C=O)O or (C=O);

Z is independently selected from the group consisting of: heteroalkyl, aryl, heteroaryl, aralkyl, alkylaryl, alkylheteroaryl, alkylether, C1-C4 alkyl, branched C3-C7 alkyl, C3-C7 cycloalkyl, C3-C7 heterocycle, and C3-C7 cycloalkane; and pharmaceutically acceptable salts thereof; with the proviso that formula (IX) is not the following compound:

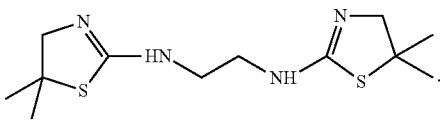

Another embodiment of the present invention provides methods of inhibiting viral recruitment and/or viral preparation of human tRNA$_3^{Lys}$; or methods of treatment of HIV disease in a patient in need thereof, comprising administration of a therapeutically effective amount of the compound selected from the group consisting of:

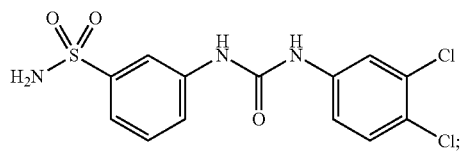

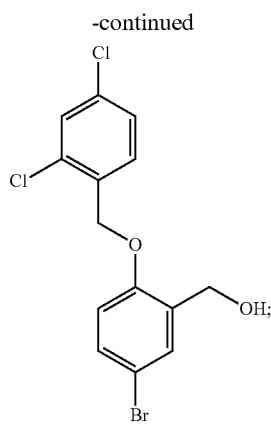

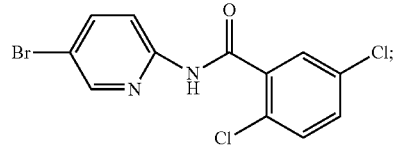

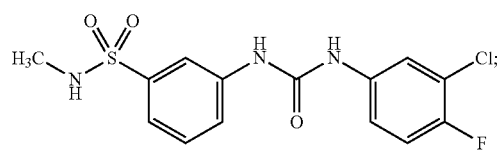

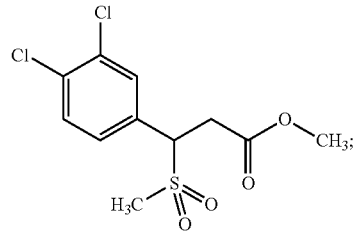

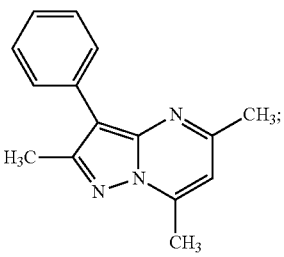

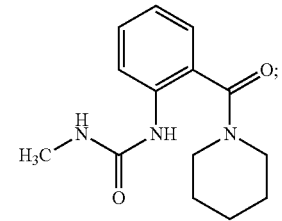

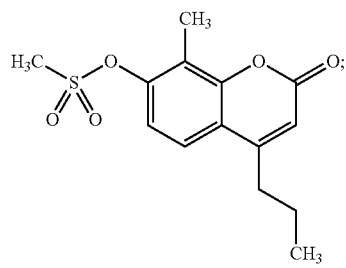

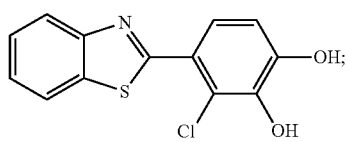

-continued

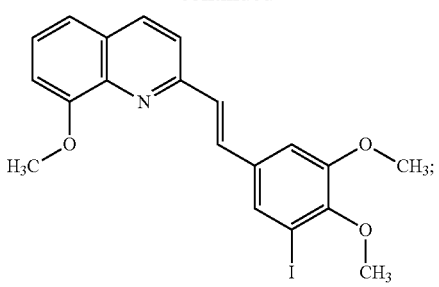

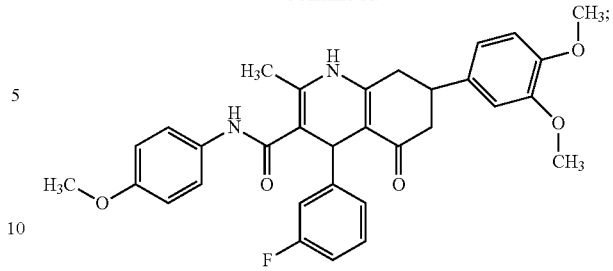

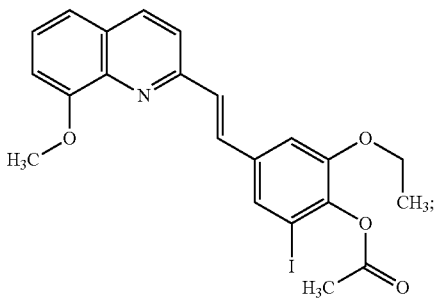

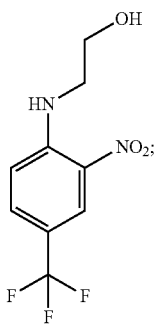

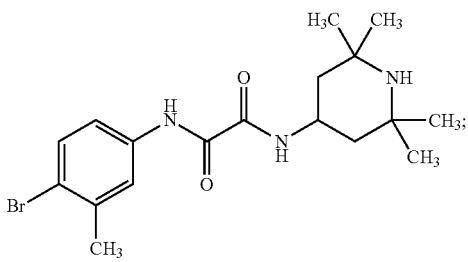

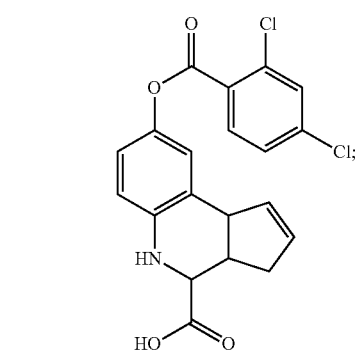

and pharmaceutically acceptable salts or analogs thereof.

Examples

This invention is further illustrated by the following examples that should not be construed as limiting. Those of skill in the art should, in light of the present disclosure, appreciate that many changes can be made to the specific embodiments which are disclosed and still obtain a like or similar result without departing from the spirit or scope of the invention.

In order to identify a set of small molecule 'hits', that inhibit viral recruitment or viral preparation of htRNA$_3^{Lys}$, the inventors developed a microtiter plate-based fluorescence assay. This mechanism based secondary (MBS) assay uses selected peptides that best mimic HIV proteins in their binding to htRNA$_3^{Lys}$. The present invention uses the above-mentioned MBS assay to identify small molecule bioactive hits against a host cell RNA interaction with HIV proteins critical to viral replication. These hits can now be optimized into a completely different class of HIV drug, one that is far less likely to elicit drug resistance. The present invention is exploiting affinity selected peptides as tools to investigate and understand RNA chemistry and structure, including naturally occurring modifications, as identity elements for HIV protein recognition of the human tRNA$_3^{Lys}$.

As mentioned above, HIV, like all retroviruses, uses a host (human) cellular tRNA as the primer for reverse transcription. HIV-1 has evolved to selectively use a very specific human tRNA, called tRNA$_3^{Lys}$, for replication. FIG. 1 depicts the life cycle of HIV and its selective use of tRNA$_3^{Lys}$. Even if the HIV-1 genome is forced through genetic manipulation to select a different tRNA, the mutated HIV-1 virus eventually reverts back exclusively to the htRNA$_3^{Lys}$ for replication (Moore-Rigdon et al., supra). Thus, the ability to block the HIV virus from selecting htRNA$_3^{Lys}$ will stop the virus from replicating. Historically, the challenge for drug discovery has been duplicating such macromolecular interactions in a cell-free system, so that large numbers of small molecules can be screened for effectiveness in blocking the RNA function. Much of the specificity of proteins and other RNAs for RNA structure resides in the distinctiveness of RNA's ability to fold into a multitude of conformations and combinations of structural motifs unique in chemistry and structure. The interaction of RNAs with proteins works well in living systems, but the complexity of the protein interaction does not stand up well in ex vivo cellular and particularly in in vitro systems.

In a relatively short time, the inventors have successfully emulated in vitro complexes of host tRNA-viral protein interactions with the use of phage affinity selected peptides (Table 1).

TABLE 1

Phage display peptide selection against hASL3LYS: in vitro/in vivo-Agris et al., 1995; Agris et al., 1999; Eshete et al., 2007; Graham et al., 2011

| Selection and characterization of peptides binding to ASLs | yeast $ASL^{Phe}$- $Cm_{32}$; $Gm_{34}$; $m^1G_{37}$; $m^6C_{40}$ | human $ASL_3^{Lys}$- $s^2U_{34}$; $\psi_{39}$ | human $ASL_3^{Lys}$- $mcm^5s^2U_{34}$; $ms^2t^6A_{37}$; $\psi_{39}$ |
|---|---|---|---|
| Synthesis of ASL with terminal biotin | ✓[a,b] | ✓[d] | ✓ |
| Phage Display Selection | ✓[b] | ✓[d] | ✓ |
| Sequencing of selected phage | ✓[b] | ✓[d] | ✓ |
| Synthesis of selected peptides | ✓[c] | ✓[d] | ✓ |
| Characterization of peptide binding | ✓[c] | ✓[d] | ✓ |
| Selection of high affinity, high specificity peptide(s) | ✓[c] | ✓[d] | ✓ |
| Validation of peptide as protein mimic | ✓[c] |  | ✓ |
| Peptide inters Cells |  |  | ✓ |
| Peptide effects RNA function | ✓[c] |  | ✓ |

Physicochemical studies of the recognition of an entire RNA by an entire protein present a number of difficulties. Large RNA structures bound by large proteins are often dynamic in solution. In contrast, peptide-RNA interactions are more readily studied, such as the Tat-Tar and Rev-RRE systems (Grate et al., *Structure* 1997, 5, 7-11; Long et al., *Biochemistry* 1999, 38, 10059-10069; Weiss et al., *Biopolymers* 1998, 48, 167-180), and include the NMR-derived structures of Rev peptide bound to RNA aptamers (Ye et al., *Chem. Biol.* 1999, 6, 657-669). Portions of proteins recognize RNAs specifically and with high affinity through "identity elements". These identity elements include both the local chemistry and conformation of the RNA, tRNA's anticodon domain is particularly distinct in chemistry and conformation. The swapping of peptide sequences has demonstrated that as little as 10 amino acids confer protein specificity for a tRNA's anticodon domain (Frugier et al., *PNAS* 1997, 94, 11291-11294). The MBS screen for HIV (described below) involves peptides of 15 and 16 amino acids in length. The peptides are sufficient in chemistry and structure to mimic that portion of a protein that binds RNA with high affinity and specificity in a functional interaction (FIG. 2). As demonstrated in FIG. 3, one example of the MBS assay is a fluorescein conjugated peptide mimic of HIV recruiting proteins.

MBS assay is based on phage display selected peptides that mimic HIV proteins by binding with high affinity and specificity to only the portion of the $htRNA_3^{Lys}$ of interest, the $hASL_3^{Lys}$ (Graham et al., *J. Mol. Biol.* 2011, 410(4): 698-715; Vendeix et al., *J. Mol. Biol.* 2012, 416(4):467-85). The $hASL_3^{Lys}$ is involved in a functional interaction with HIV protein(s), such as the nucleocapsid protein NCp7 (or NC) (FIG. 2). The small size of MBS model system is a technological advantage. The complex of peptide and $hASL_3^{Lys}$ is ~7000 Daltons. The high-affinity peptide is synthesized with a fluorescent tag as a reporter of binding. See FIG. 3. The RNA is synthesized in its native sequence with post-transcriptional modified nucleosides. The small length and chemical synthesis produces RNA of the exact sequence with site-selected incorporation of native modifications precluding the problems inherent in RNA transcription in vitro. The MBS assay is readily amenable to thermodynamic and structural analyses and nucleotide and peptide amino acid changes for optimization. Hits are identified from thousands of small molecules by virtue of their abilities to inhibit at low concentration and high specificity the binding of the fluorescent peptide to the target RNA. The inhibition of the fluorescent peptide from binding $hASL_3^{Lys}$ is depicted in FIG. 3.

It has been demonstrated repeatedly that 15 and 16-amino acid peptides are selected from a random phage display libraries using the criterion of binding to a modified, rather than unmodified, ASL (Agris et al., *J. Protein Chem.* 1999, 93, 10063-10068; Mucha et al., *Acta Biochim. Pol.* 2003, 50, 857-864; Mucha et al., *Protein* 2003, 23, 33-38 Mucha et al., *RNA* 2002, 8, 698-704; Mucha et al., *Biochemistry* 2001, 40, 14191-14199). This has been particularly successful with the fully modified $hASL_3^{Lys}$ (FIG. 4—(Eshete et al., *The Protein J.* 2007, 26, 61-73; Graham et al., supra).

This unique technology can be exploited to target the essential recruitment of human $tRNA_3^{Lys}$ ($htRNA_3^{Lys}$) by the HIV poly-protein, Gag, polymerase and the nucleocapsid protein, NCp7 (Kleiman et al., *Int. J. Biochem. Cell Biol.* 2004, 36, 1776-1778). Significantly, $tRNA_3^{Lys}$ is concentrated within the HIV capsid by these HIV proteins, possibly with the aid of lysyl-tRNA synthetase (Beuning et al., *Biopolymers* 1999, 52, 1-28; Kleiman et al., *FEBS Lett.* 2010, 584, 359-365). The 15 to 16 amino acid peptides that have been used in assays to screen and select small molecules that bind to the tRNA have been shown to have properties that are characteristic of the HIV nucleocapsid protein (Graham, et al 2011). Thus, these peptides maybe mimicking host (human) proteins recruited by the HIV infection to facilitate the replication, integration or structural needs of the virus. The HIV proteins specifically recruit $htRNA_3^{Lys}$ in competition with the cell's protein synthesizing machinery (FIG. 2). NCp7 denatures the $htRNA_3^{Lys}$ (Beuning et al., supra and facilitates annealing of the 3' side of the tRNA's amino acid accepting stem and ribothymidine stem to the primer binding site (PBS) and the highly modified anticodon domain to the A-rich. Loop 1 of the HIV genome (Marquet et al., *Biochimie.* 1995, 77, 113-124; Lanchy et al., *Biochimie.* 1996, 78, 1087-1096; Brule et al., *Nucleic Acids Res.* 2000, 28, 634-640) (FIG. 2). The post-transcriptional modifications of the primer $htRNA_3^{Lys}$ are important for HIV replication (Marquet et al. supra). Even with alterations at both the viral PBS and the viral A-rich Loop 1, at which the U-rich $htRNA_3^{Lys}$ anticodon domain binds, the virus capsid is enriched with $htRNA_3^{Lys}$ (Sundaram et al., *Biochemistry* 2000, 39, 12575-12584). With such a dedication to $htRNA_3^{Lys}$ and the tRNA's role in decoding the genome, it is expected that the generation of strains resistant to therapeutics that inhibit $htRNA_3^{Lys}$ recruitment and/or viral preparation (denaturation) would be minimized. Thus, the identification of small molecules as leads that inhibit the recruitment of $htRNA_3^{Lys}$ as the primer of HIV RT has the novelty of targeting an almost immutable and critical function in HIV replication.

Optimization of the MBS Assay

The phage-display selection of peptides was completed (randomized 15 mers, and 16 mers with cysteines at two sites for the possible generation of $Zn^{+2}$ 'knuckles' structures reminiscent of the HIV protein, NCp7) against the fully modified anticodon stem and loop domain of $htRNA_3^{Lys}$ with 5-methoxycarbonylmethyl-2-thiouridine at position 34, 2-methylthio-$N^6$-threonylcarbamoyladenosine-37 and pseudouridine-39 ($hASL_3^{Lys}$-$mcm^5s^2U_{34}$;$ms^2t^6A_{37}$;$\Psi_{39}$) covalently attached to microtiter avidin-plates with biotin. In reiterative and competitive phage-display library selections, the two libraries yielded 20 recurring peptide sequences that had reasonable solubility among 155 sequenced clones (Table 2). The $hASL_3^{Lys}$ binding properties of the peptides were characterized using chemically synthesized peptides with an N-terminal fluorescent reporter. One strongly binding, highly specific peptide (P6) was selected. Its ability to mimic the binding of the natural HIV protein, NCp7, to modified htRNA$_3^{Lys}$ was validated. P6 mimicked NCp7 in binding the fully modified hASL$_3^{Lys}$ (FIGS. 5 and 6) with a high affinity (Kd=0.45±0.05 vs. 0.28±0.03 µM, respectively) and modification-dependency (with unmodified ASL$_3^{Lys}$, Kd=incalculable). It was also observed with circular dichroism (CD) that both P6 and NCp7 denature the hASL$_3^{Lys}$ structure (FIG. 7) (Graham et al., supra). The progressive decrease in CD ellipticity with the addition of increasing amounts of P6 or NCp7 indicated that in binding to hASL$_3^{Lys}$, the peptide and NCp7 reduced base stacking drastically. In contrast to the hASL$_3^{Lys}$ which was a stable hairpin, CD and NMR studies indicated that the peptide had no structure in solution (not shown). Footprinting of P6 on the modified hASL$_3^{Lys}$ by high resolution mass spectrometry indicated conclusively that the anticodon and 3'-adjacent side of the loop were protected (Graham et al., supra). This result was consistent with P6 binding the hASL$_3^{Lys}$ with the immature modification t$^6$A$_{37}$ with higher affinity than the unmodified ASL.

TABLE 2

| Peptide | 15 and 16 Amino add | Library/Elution |
| --- | --- | --- |
| 1 | FSVSFPSLPAPPDRS | Fuse5/basic |
| 3 | GRVTYYSCGVSLLFQ | Fuse5/basic |
| 4 | AGPVPLHSLSYYYNQ | Fuse5/basic |
| 5 | RAVMTVVWPVSFAGF | Fuse5/acidic |
| 6 | RVTHHAFLGAHRTVG | Fuse5/acidic |
| 8 | PAVASTSSLIIDGPF | Fuse5/acidic |
| 9 | PKAFQYGGRAVGGLW | Fuse5/acidic |
| 10 | AAHVSEHYVSGSLRP | Fuse5/acidic |
| 11 | ASVGPAPWAMTPPVS | Fuse5/acidic |
| 12 | APALWYPWRSLLPLY | Fuse5/acidic |
| 13 | ASLHPVPKTWFFLLS | Fuse5/acidic |
| 14 | WSHSRNTADVPVSML | Fuse5/acidic |
| 15 | HRGYCRDRWNCGEYF | F88-cys6/basic |
| 17 | PHRQCSAPAKSCKILP | F88-cys6/basic |
| 19 | TLPACHELPKHCKRRG | F88-cys6/basic |
| 20 | TLPACHELPKHCNEAR | F88-cys6/basic |
| 21 | NGPECNAYMVRCRGYH | F88-cys6/basic |
| 23 | GNSNCPMLNEQCPWQD | F88-cys6/basic |
| 24 | HTETCINIRNTCTTVA | F88-cys6/basic |
| 25 | LKLPCKITINNCQLAG | F88-cys6/basic |

Peptide selected by phage display

The hypermodifications (mcm$^5$s$^2$U$_{34}$) and (ms$^2$t$^6$A$_{37}$) include hydrophilic moieties, an ester, an alcohol and free acid, respectively. The modifications are within ~12 Å of each other and are thus, easily bridged by an interacting small molecule (FIG. 8). Once submerged in the small molecule interaction, the identity of the anticodon would no longer be recognizable by HIV proteins. If the htRNA$_3^{Lys}$ were recruited by HIV proteins, the interacting small molecule still would preclude the annealing of the anticodon to the HIV Loop 1 thereby, blocking HIV's ability to recruit, transport, denature and/or anneal the tRNA to the viral genome.

The MBS assay was improved for maximum sensitivity and minimum use of reagents, 1 µM and 0.5 µM of hASL$_3^{Lys}$ and P6 respectively, and assay volume reduced from 300 µL to 15 µL. As a result, the reagents cost has also been minimized. The phosphate buffer (20 µM), pH=6.8 and salt concentration (40 µM) were optimized. With a Janus robot (PerkinElmer) and an EnVision microplate reader (PerkinElmer), the assay volume and thus the reagents are considerably reduced allowing to perform 20 times as many experiments with the same amount of reagents.

Level 1 Screen

First, an in silico Level 1 Screen of the 20,000 small molecule library was conducted followed by a HIV-infected, cell-based assay. This change in the approach was more efficient, saved time and expensive materials (specifically modified hASL$_3^{Lys}$), than a comprehensive MBS assay Level 1 Screen in vitro. The goal was to produce more predicative results earlier in the screening process and obviate the need for the in vitro fluorescence MBS assay using 20,000 small molecules. With the three dimensional NMR and X-RAY structures of the target (i.e. hASL$_3^{Lys}$-mcm$^5$s$^2$U$_{34}$;ms$^2$t$^6$A$_{37}$;Ψ$_{39}$) known, it was envisioned using computational and structural approaches (Stroud et al., *Computational and Structural Approaches to Drug Discovery Ligand-Protein Interactions*, 2007, RSC publishing) to identify potentially active molecules. A molecular docking protocol (MDS) that was then used to perform a virtual screen (VS) of library of 20,000 small molecules. AutoDock Vina (Trott et al., *J. Comput. Chem.* 2010, 31, 455-461) was employed as a computational tool that combines a search algorithm to generate putative binding modes of the small molecules (the ligands) into the hASL$_3^{Lys}$ (the receptor and target) with a scoring function that ranks them. This allowed to identify and select approximately 1,000 small molecule hits having a high binding affinity (~6.0 Kcal/mol) for the hypermodifications (mcm$^5$s$^2$U$_{34}$) and (ms$^2$t$^6$A$_{37}$) present within the loop region of the hASL$_3^{Lys}$ (FIG. 8). FIG. 9 provides a schematic diagram of how a small molecule hit in the cell-based assay disrupts the HIV life cycle.

Five hundred of the 1000 small molecule hits, having the highest binding affinity with the ASL's hypermodifications, were selected for screening at high concentration against HIV infected mammalian cells (FIG. 10). Briefly, toxicity was first assessed in 293T cells in 96-well plates (10$^4$ cells/well) by adding 50, 5 and 0.5 µM of small molecules in triplicate at each concentration. After two days, cells were assessed for poor growth versus control cells. Once the concentration of the small molecules at which the cells looked normal was established, these molecules were screened for anti-HIV activity through a transfection/infection protocol. An infectious molecular clone of HIV (strain NL4-3) was transfected into 293T cells using FuGene6 (Roche). After four hours, the cells were split into 96-well plates (10$^4$ cells/well) and the small molecules were added at the appropriate concentration in triplicate. After 48 hours of incubation of cells in the presence of the small molecules, virus-containing medium (50 µL) was removed from each well and transferred into a fresh 96-well plate containing TZM-bl cells for infection (10$^4$ cells/well). After 48 hours, the cells were assayed for luciferase expression. Controls were untransfected 293T cells and transfected cells without the small molecules added. Results from various small molecules with the best inhibition of HIV are shown in (FIG. 10). Active small molecules 2493, 9324, 8317, 2725, 3643, 2491, 12327, 14094, 12204, 12744, 12745, 12542, 18198, 18200, 8391, 6188, 16286 and 2712 have 80-95% inhibitory effect on the HIV propagation. These small molecules with bioactivity against HIV propagation are an example of some the hits further tested in a concentration-dependent screening.

Level 2 Screen

Figure 12B:
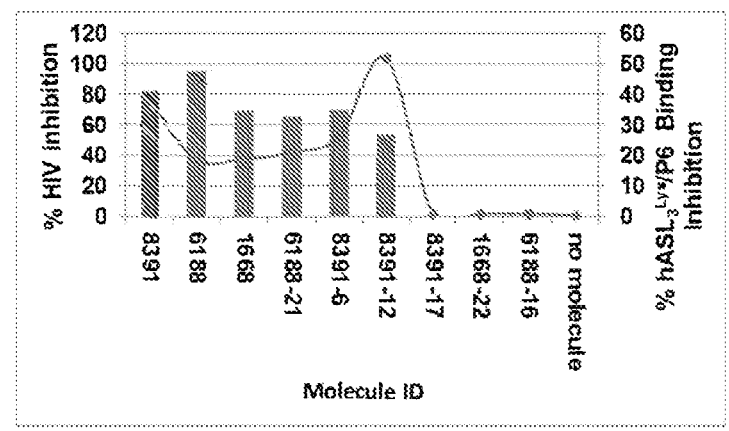

Bioactive molecules selected in Level 1 Screen were tested using the cell based assay in a concentration (dose)-dependent manner for their ability to inhibit HIV propagation (FIG. 11). The HIV cell based assay experimental protocol described in Level 1 screen was used to conduct the Level 2 Screen. The results (FIG. 11) showed that molecules 18200, 6188, 16286, 2712 and 8391 inhibited the HIV propagation at concentrations from 5-50 µM. In addition to the concentration-dependent, cell based assay, the inhibitory activities of the active molecules identified in Screen Level 1 were also assessed using the MBS assay. This assay has been developed and standardized to mimic the unique properties characteristic of the HIV viral protein recruitment and preparation of the human host tRNA$_3^{Lys}$ as primer of reverse transcription. Thus, the cell-based assay and the "MBS" assay were used to confirm the mechanism of action of the hits against the functional interaction of htRNA$_3^{Lys}$ with HIV proteins. The MBS is a "mix and measure" assay that consists of the formation of a complex between the fluorescent peptide P6 and the fully modified anticodon stem and loop of htRNA$_3^{Lys}$. The concentration of the small molecules was 150 µM i.e. 300 fold of that of P6. The results showed that upon complex formation between the fluorescein-tagged P6 and hASL$_3^{Lys}$-mcm$^5$s$^2$U$_{34}$;ms$^2$t$^6$A$_{37}$;$\Psi_{39}$ and in the absence of small molecules, the hASL$_3^{Lys}$ quenched the fluorescence of the fluorescein-tagged P6 by ~80% as expected. In the presence of various selected active molecules, inhibition of the complex between P6 and hASL$_3^{Lys}$ was observed (FIGS. 12 A, B and C). The results of these experiments allowed identification and concentration towards a smaller pool of active molecules.

In order to confirm the activity of the small molecules showing potential anti-HIV inhibition, a second round of testing using their analogs (~20 analogs were chosen for each selected active small molecule) was initiated using the same cell based assay employed in Level 1 Screen and Level 2 Screen. Some of the results, presented in FIGS. 12 A, B, and C, indicate that compounds 6188, 1668-17, 1668-18, 18200, 18200-2 and 18200-3 are some of the most bioactive inhibitors. Other derivatives, 1668-12 and 8391-5, also showed potential anti-HIV inhibition. The quality and structure of the small molecule hits and their respective analogs were confirmed by NMR and Liquid Chromatography coupled with Mass Spectrometry (LC-MS).

HIV Strain Screening

Small molecules were also screened for their effectiveness against various HIV strains. For example, the effects of small molecules of interest on HIV strains NLA3, HXB and JR-CSF were studied. See FIG. 13. Compound 1668-18 was particularly effective for inhibiting infection of all three strains relative to no addition of drug. FIG. 13. Further, small molecules were screened for their effectiveness against other HIV drugs that have different modes of action. For example, various small molecules of interest in the initial screen were studied for their effectiveness relative to protease inhibitors (Saquinavir by Roche) and reverse-transcriptase inhibitors (Nevirapine by Boehringer Ingelheim) against various strains, including tri-therapy resistant HIV strains. FIGS. 13 and 14. In one specific study, the effect of small molecules on cell culture HIV viral propagation was compared to no drug (by reviewing % Relative Luminescence Unit (RLU)). Small molecules were also compared to Saquinavir and Nevirapine in both standard HIV strain and Tri-therapy resistant HIV strains. FIG. 14.

Furthermore, the small molecules of the present application provide minimal to no toxicity to human cells in culture at small molecule concentrations capable of inhibiting HIV-1 replication compared to the absence of these small molecules. In one embodiment of the invention, the small molecules provide minimal to no toxicity to human cells in culture at small molecule concentrations capable of inhibiting HIV-1 replication by at least about 60%, when compared to the absence of these small molecules. In another embodiment of the invention, the small molecules provide minimal to no toxicity to human cells in culture at small molecule concentrations capable of inhibiting HIV-1 replication by at least about 70%, when compared to the absence of these small molecules. In another embodiment of the invention, the small molecules provide minimal to no toxicity to human cells in culture at small molecule concentrations capable of inhibiting HIV-1 replication by at least about 80%, when compared to the absence of these small molecules. In another embodiment of the invention, the small molecules provide minimal to no toxicity to human cells in culture at small molecule concentrations capable of inhibiting HIV-1 replication by at least about 90%, when compared to the absence of these small molecules. In another embodiment of the invention, the small molecules provide minimal to no toxicity to human cells in culture at small molecule concentrations capable of inhibiting HIV-1 replication by about 60% to about 99%, when compared to the absence of these small molecules. In another embodiment of the invention, the small molecules provide minimal to no toxicity to human cells in culture at small molecule concentrations capable of inhibiting HIV-1 replication by about 60% to about 90%, when compared to the absence of these small molecules. In another embodiment of the invention, the small molecules provide minimal to no toxicity to human cells in culture at small molecule concentrations capable of inhibiting HIV-1 replication by about 85% to about 95%, when compared to the absence of these small molecules.

Specificity Screening

To determine whether the action of these active small molecules and analogs was specifically to disrupt the htRNA$_3^{Lys}$ binding to the viral RNA in the virus, intravirion reverse transcription from the bound tRNA was assessed directly. Virions in the medium after 293T transfection were assayed in an endogenous reverse transcription reaction using techniques (Kaushik et al., *Nucleic Acids Res.* 2001, 29, 5099-5106; Warrilow et al., *PLOS. One* 2010, 5, e13229). The virus was precipitated from the medium using a 20% PEG/0.2M NaCl solution (1 volume added to 4 volumes medium) at 4° C. overnight. The precipitated virus was harvested by centrifugation and the viral pellet was re-suspended in a Tris/MgCl$_2$/Triton X-100 buffer. 20 µCi of $^{33}$P-dCTP and 20 mM of each of the other dNTPs were added to the mixture and it was incubated for 30 min at 37° C. The reaction was stopped with 20 mM EDTA and the RNA/DNA molecules were isolated using a miRNeasy kit from Qiagen. The extracted reverse transcription reactions were separated on a 6% denaturing acrylamide gel and detected by phosphorimaging; two bands that were larger than 400 nt were quantified using ImageQuant software. P24 in the viral supernatants was determined by ELISA assay using a 1:50 dilution. The results indicate that at least eight molecules (6188, 6188-14, 18200-1, 8391-15, 18198, 14094, 12327, 9324 and 3902 may have specific htRNA$_3^{Lys}$ binding inhibitory activity (FIG. 15). In contrast, using a similar technique, there was little to no effect on MLV (murine leukemia virus) propagation in cell culture. FIG. 16. In another indication of the small molecules establishing specific htRNA$_3^{Lys}$ binding inhibitory activity, Saturation Transfer Difference (STD) NMR Spectroscopy was performed. STD-NMR enables detection of the presence of binding equilibriums and identifies protons of hit small molecules in direct contact with the modified hASL$_3^{Lys}$ (Mayer et. al. 1999). As an example, the observed NMR line broadening and the chemical shift changes (Δδ=0.3 ppm) indicate a strong and specific affinity between 8391 and the modified hASL$_3^{Lys}$ as opposed to the unmodified for which minor changes were detected. See, e.g., FIG. 17. Small molecules are added during stage 2 of the HIV life cycle (FIG. 1 of the HIV Life Cycle) corresponding to Integration, Transcription, Translation and Assembly that yields newly formed infectious virus. Since luciferase signals (RLU values on FIG. 18) at Stage 2 are detected at the same level compared with the no drug control, hit small molecules do not inhibit HIV gene expression (which includes luciferase expression) that occurs only if Integration, Transcription and Translation of the viral DNA and RNA take place. When hits are added to the infected human tissue cultures during Stage 1 of the virus life cycle i.e., Entry, Uncoating and Reverse Transcription, no anti-HIV effect is observed. Therefore, the above results demonstrate that unlike current commercial anti-HIV drugs i.e., Integrase, Reverse Transcriptase and Protease Inhibitors, the hit small molecules of the present invention inhibit viral Assembly. Accordingly, this further supports the mechanism that the small molecules specifically disrupt the htRNA$_3^{Lys}$ binding.

Optimization of the Active Molecules

MBS assay and HIV cell based assays will be used to eliminate molecules for which apparent activity is due to factors other than the desired interaction with the modified ASL$_3^{Lys}$. The selective mode of action of active molecules will be assayed in the presence of competing non-specific RNAs or DNA molecules using an optimized fluorescence screening method. The auto fluorescence property of the molecules will be measured in the assay buffer (phosphate). A cell based assay will also be carried out using a target-null system i.e., a retrovirus in which the target (hRNA$_3^{Lys}$) is absent, e.g., XMRV virus.

Dose response data of the active molecules were generated by running the biochemical and functional assays at varying concentration. The potency properties which is one of the characteristics that defines a hit, is evaluated based on the criteria that potency (IC50)<3 µM in the MBS assay and EC50<10 µM in the HIV cell based assay (See FIG. 19). The molecules that meet these criteria will be further evaluated.

The physicochemical characteristics of the active small molecules are important parameters that will require optimization further. Therefore preliminary evaluation of these characteristics will help identify the deficiencies and enable head to head comparison of individual active series. Structural rules such as those of Lipinski and Veber provide guidance for cell-permeable orally bioavailable drugs, <5H bond donors, molecular weight <500, <10 H bond acceptors and lipophilicity c log P<5; and molecular flexibility-rotatable bonds ≤10, polar surface area-PSA≤140 Å and H-bond count ≤12 total acceptors plus donors (Lipinski et al. *Adv. Drug Deliv. Rev.* 2001, 46, 3-26). Ideally, the optimal hits would have lower molecular weight, lower lipophilicity, and fewer H bond donors or acceptors. Typically, during the course of optimization in the hit-to-lead and lead optimization phases, the molecule is built out from the hit scaffold to enhance activity and selectivity. Measures of lipophilicity (c Log P) and PSA generally are directly related to physicochemical properties like aqueous solubility and affect the extent of plasma protein binding to the drug molecule and hepatic stability (metabolism by cytochrome P450 enzymes). During the course of the SAR exploratory phase, in-silico calculation of ADMET parameters will be used to guide molecule selection and design.

Once the hit series is sufficiently profiled against the criteria outlined above, the prioritization between different chemotypes should be possible, thereby enabling allocation of resource and methods to optimize the hit series with the highest likelihood of furnishing a lead series in an appropriate time frame. Depending on the nature (e.g. MW, drug-like profile, chemical groups present in the structure) of the selected hits, the hit-to-lead process will involve techniques such as hit evolution, (bio)isosteric replacements and hit fragmentation, or any combination of these. In the hit evolution, analogs of the original hits will be synthesized with different substitution patterns and tested using the MBS and the HIV cell based assays. Initial SAR data produced by these synthesized analogs will then be used to drive exploratory medicinal chemistry efforts. Alternatively, (bio)isosteric replacements will be used. This method is useful for improving the hit profile while maintaining potency. In the case of hits with large MW are identified, Hit fragmentation techniques will be applied. This method will consist of the structural decomposition of active hits that leads to the identification of promising fragments or minimum pharmacophores.

The identification of the minimal core fragments could then serve as a new starting point for fragment expansion. Fragmentation could also be followed by the combination of fragments identified even in different hits.

The oral administration route is considered to be optimal (Rankovic et al., *Approaches in Drug Discovery*, 2010, John Wiley & Sons, Inc.) for small-molecule delivery as it allows a wide range of doses to be administered, allows convenient patient self-administration, is adaptable to varying dosage regimens and needs no special equipment. Therefore, this program will seek to discover orally available clinical candidates. Thus it is important to determine the required optimal parameters for oral absorption at this stage. The optimized hits (lead molecules) will need to be absorbed by transcellular route and thus will need to possess a requisite degree of membrane permeability. Permeability is central to ADME properties defining absorption and rapid equilibrium between tissues, cell interior, and the circulating unbound fraction in the plasma (Rankovic et al., supra). Three physicochemical properties have been closely associated with permeability, Molecular Weight (MW), lipophilicity (c log P/log D) and polar surface area (PSA) (Palm et al., *Pharm. Res.* 1997, 14, 568-571).

The objectives of the screening will be to determine the ADME properties for oral bioavailability: dissolution, adequate transfer across the membranes of gastrointestinal tract, and low clearance/metabolic stability. This task will also begin to establish whether available optimized hits have the potential to be modified to produce development lead molecules.

The permeability will be tested using Caco-2 cell system. There could be considerable discussion as to which cell system to use for absorption or permeability screening e.g.

Caco-2 vs. MDCK. It is believe that the more important than the actual cell type used is rigorous standardization of the experimental conditions (Volpe D. A. *J. Pharm. Sci.* 2008, 97, 712-725). Repeat evaluation of standard reference molecules will be used to help interpret the results. We exclude the use of PAMPA (Parallel Artificial Membrane Penetration Assay) because it is a poorly characterized system and the extrapolation to in vivo absorption system is rather difficult. Caco-2 cell model's accuracy is considered >80-85%. This will primarily provide a rank ordering of molecules regarding their human absorption.

For measuring the transepithelial transport of our selected hit molecules, standard protocols will be followed (Li, A. P. *Drug Discovery Today* 2001, 6, 357-366. The optimized hits molecules will be expected to have a value of apparent permeability coefficient $P_{app} > 1 \times 10^{-5}$ cm/s that is characteristic of a complete absorption. The metabolic stability study will allow optimization of the pharmacokinetic parameters (e.g. bioavailability and clearance in vitro and in vivo) of the hits and to determine the percentage of molecule hits lost over time in the presence of a metabolically active test system such as microsomes and hepatocytes. The metabolic property will need to be assessed with commonly used protocols throughout the pharmaceutical industry (Ackley et al., *Optimization in Drug Discovery*, 2004, Humana Press, 151-162. The optimized pharmacokinetic parameters will allow establishing a correlation between in vitro and in vivo stability. For more details about the protocols that will be used as a template refer to Ackley et al., supra. To qualify as leads, the molecule hits should show an intrinsic clearance <25 µL/min/mg in oxidizing human microsomes or <10 µL/min/$10^6$ cells in oxidizing cells in human hepatocytes. In the case of oxidizing rat microsomes or hepatocytes one should expect a clearance <40 µL/min/mg or 15 µL/min/$10^6$ cells respectively.

The selected hit molecules will be screened for P450 inhibition using a well-developed high throughput screening (HTS) (Miller et al. *Ann. N.Y. Acad. Sci.* 2000, 919, 26-32) assay. Hit molecules will be incubated with microsomes in the presence of P450 substrates that enable metabolism to be quantified using fluorescence.

Although genetically engineered microsomes enable HTS for P450 inhibition, the generated data might need confirmation using human liver microsomes that contain all of the P450 isoforms in a human liver. Hit molecules could be metabolized by one isoform to metabolites that might be more or less effective at inhibiting another P450 isoform. In this assay, hit molecules will be incubated with liver microsomes in the presence of various isoform specific substrates (Rodrigues et al., *Adv. Pharmacol.* 1997, 43, 65-101. The formation of metabolites representing the activity of specific isoforms will be then quantified using HPLC or LC-MS.

Screening for inductive DDIs will be achieved by using HTS for CYP3A4 (testosterone) since the induction of this hormone has been well defined Lehmann et al., *J. Clin. Invest.* 1998, 102, 1016-1023. Hit molecules that will induce CYP3A4 will activate the pregnane-X-receptor (PXR), which will bind to a response element in the CYP3A4 pregnane-X-receptor gene response element (PXRE) (Lehmann et al., supra). The HTS assay for CYP3A4 will consist of using a genetically engineered cell line that expresses a PXRE-luciferase reporter gene (Moore et al., *Retrovirology* 2005, 2, 21). Induction of CYP3A4, by the xenobiotic-mediated binding of PXR to PXRE, will lead to the activation of luciferase synthesis, which can be quantified using for example a chemiluminescent substrate such as luciferin.

The toxicity, which is another determinant in the selection of optimized hit molecules, will be evaluated for progression. It is acknowledged that the toxicity is arguably the most difficult drug property to adequately screen, because it could be species-specific, organ-specific, and could involve multiple host factors and chronic dosing regimens, all of which cannot be adequately modeled experimentally. However, as hepatotoxicity is a major manifestation of drug toxicity, and it is known that toxicity can be influenced by drug metabolism. Therefore, screening for toxicity will be adopted by using intact hepatocytes which is a well-established approach (Li, A. P. *In Vitro Toxicology*, 1994, Raven Press, New York, pp. 195-220). Briefly, screening assay for hepatotoxicity will be achieved as follows: Hepatocytes will be treated with the hit molecules and cell viability will be determined using various endpoints. The endpoints that will be used will include: quantification of ATP content, release of cytoplasmic enzymes, mitochondrial functions, dye uptake, macromolecular synthesis and cellular glutathione content (Li, A. P. supra). For screening assays, the cytotoxicity will be studied using multiple concentrations, enabling the determination of dose-response curves and $EC_{50}$ values.

The hERG channel allows for the rapid efflux of potassium ions from the cell, which is required for repolarization of the heart ventricles in preparation for the next cardiac cycle. This channel has a promiscuous nature in binding many drugs with considerable structure diversity that induces its blockage. A direct block of the hERG channel by non-antiarrhythmic drugs is a major cause of prolongation of the QT interval, potentially leading to ventricular arrhythmia or other adverse cardiovascular effects such as torsades de pointes (TdP). Therefore, the affinity of the hit molecules to the hERG (human Ether-à-go-go Related Gene) ion channel will be assessed by screening the hit molecules for channel affinity and selectivity for $htRNA_3^{Lys}$. This will be performed first using a cost effective in silico model such as DEREK (Sanderson et al., *Hum. Exp. Toxicol.* 1991, 10, 261-273. The in vive models (Diaz et al., *J. Pharmacol. Toxicol. Methods* 2004, 50, 187-199; Wible et al., *J. Pharmacol. Toxicol. Methods* 2005, 52, 136-145 that are technically demanding, costly and labor intensive will be used in the early stage of the lead optimization phase. Molecules that are basic, ionized at physiological pH and having areas of lipophilicity surrounding the basic center will not be selected as molecule leads. These studies are expected to generate one or more optimized lead molecules available for future optimization and animal efficacy studies, meeting the following criteria: the in vivo pharmacokinetic (PK) study to show a clearance (Cl)<50% of liver blood flow; an oral bioavailability (F)>10%; a half-life ($t_{1/2}$)>0.5 hours; volume of distribution (Vd)>10 L/kg; oral exposure (AUC)>2,000 h·ng/mL; $t_{max}$>3 hours.

Active Compounds

Several classes of active compounds were identified using both Level I Screen as well as Level 2 Screen. These are commercially available compounds. Alternatively, these compounds can be synthesized by any of the known methods in the skill of art. The IC50 values of the selected active hit molecules were determined following NCGC (NIH) guidelines and were found to vary between 140-400 µM (MBS assay) and 3.0-75.0 µM (CFAR assay).

A. Hydroxyacetamide Inhibitors

| Compound No | Structure | Name | IC 50 (units) |
|---|---|---|---|
| A1 1668-1 | 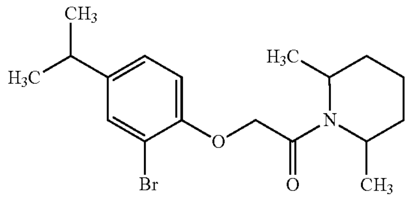 [SMILES: CC(C)c1ccc(OCC(=O)N2C(C)CCCC2C)c(Br)c1] | 2-(2-bromo-4-isopropylphenoxy)-1-(2,6-dimethylpiperidin-1-yl)ethanone | 34 |
| A2 1668-2 | 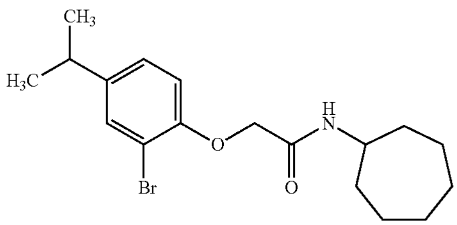 [SMILES: CC(C)c1ccc(OCC(=O)NC2CCCCCC2)c(Br)c1] | 2-(2-bromo-4-isopropylphenoxy)-N-cycloheptylacetamide | |
| A3 1668-3 | 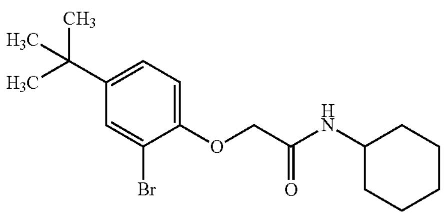 [SMILES: CC(C)(C)c1ccc(OCC(=O)NC2CCCCC2)c(Br)c1] | 2-(2-bromo-4-tert-butylphenoxy)-N-cylohexyacetamide | |
| A4 1668-4 | 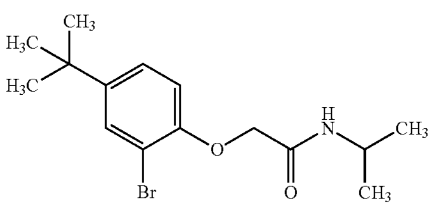 [SMILES: CC(C)NC(=O)COc1ccc(C(C)(C)C)cc1Br] | 2-(2-bromo-4-tert-butylphenoxy)-N-cyclohexyacetamide | |
| A5 1668-5 | 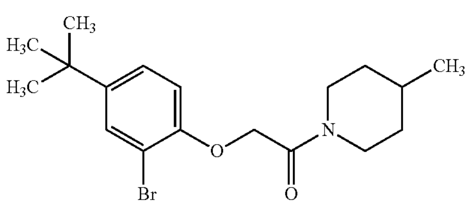 [SMILES: CC1CCN(C(=O)COc2ccc(C(C)(C)C)cc2Br)CC1] | 2-(bromo-4-tert-butylphenoxy)-1-(4-methylpiperidin-1-yl)ethanone | |
| A6 1668-6 | 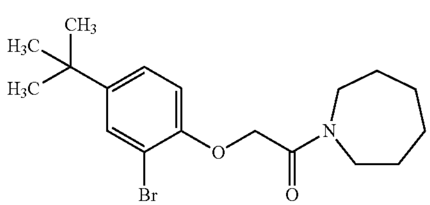 [SMILES: CC(C)(C)c1ccc(OCC(=O)N2CCCCCC2)c(Br)c1] | 1-(azepan-1yl)-2-(2-bromo-4-tert-butylphenoxy)ethanone | |
| A7 1668-7 | 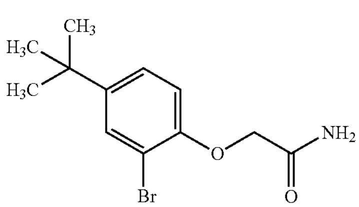 [SMILES: CC(C)(C)c1ccc(OCC(N)=O)c(Br)c1] | 2-(2-bromo-4-tert-butylphenoxy)acetamide | |

-continued

| Compound No | Structure | Name | IC 50 (units) |
|---|---|---|---|
| A8 1668-8 | 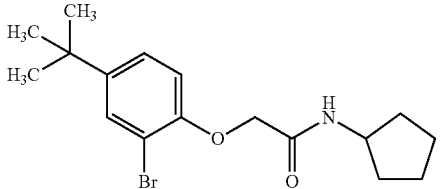 [SMILES: CC(C)(C)c1ccc(OCC(=O)NC2CCCC2)c(Br)c1] | 2-(2-bromo-4-tert-butylphenoxy)-N-cyclopentylacetamide | |
| A9 1668-9 | 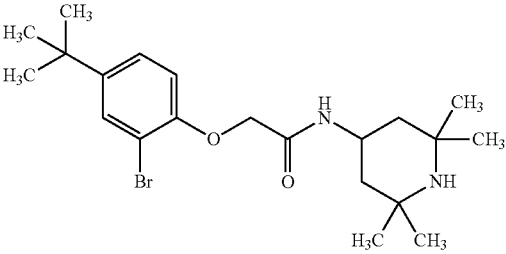 [SMILES: CC1(C)CC(NC(=O)COc2ccc(C(C)(C)C)cc2Br)CC(C)(C)N1] | 2-(2-bromo-4-tert-butylphenoxy)-N-(2,2,6,6-tetramethylpiperidin-4-yl)acetamide | |
| A10 1668-10 | 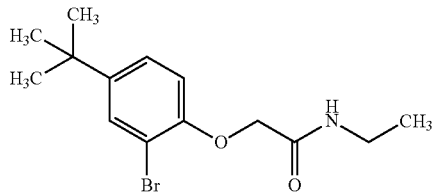 [SMILES: CCNC(=O)COc1ccc(C(C)(C)C)cc1Br] | 2-(2-bromo-4-tert-butylphenoxy)-N-ethylacetamide | |
| A11 1668-11 | 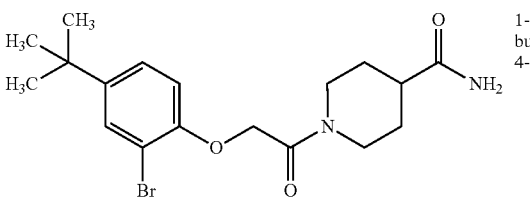 | 1-(2-(2-bromo-4-tert-butylphenoxy)acetyl)piperidine-4-carboxamide | |
| A12 1668-12 | 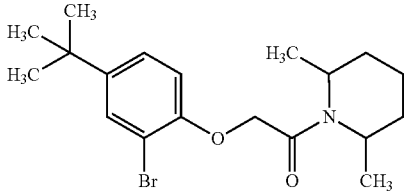 [SMILES: CC1CCCC(C)N1C(=O)COc1ccc(C(C)(C)C)cc1Br] | 2-(2-bromo-4-tert-butylphenoxy)-1-(2,6-dimethylpiperidin-1-yl)ethanone | |
| A13 1668-14 | 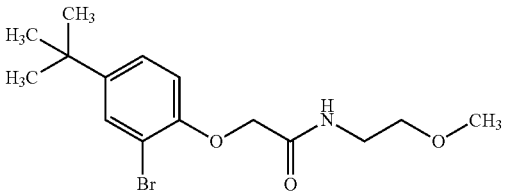 [SMILES: COCCNC(=O)COc1ccc(C(C)(C)C)cc1Br] | 2-(2-bromo-4-tert-butylphenoxy)-N-(2-methoxyethyl)acetamide | |
| A14 1668-13 | 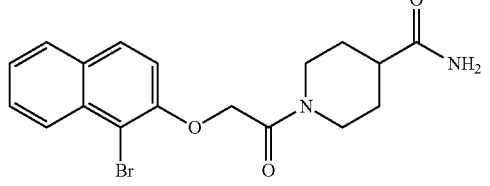 | 1-(2-(1-bromonapthalen-2-yloxy)acetyl)piperidine-4-carboxamide | |

-continued

| Compound No | Structure | Name | IC 50 (units) |
|---|---|---|---|
| A15 1668-16 | 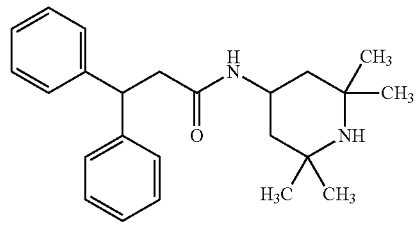 [SMILES: CC1(C)CC(NC(=O)CC(c2ccccc2)c2ccccc2)CC(C)(C)N1] | 3,3-diphenyl-N-(2,2,6,6-tetramethylpiperidin-4-yl)propanamide | |
| A16 1668-17 | 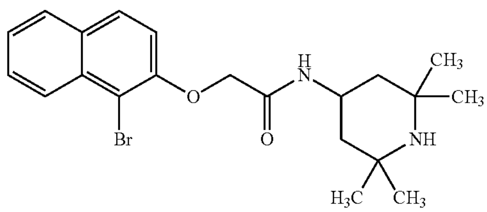 [SMILES: CC1(C)CC(NC(=O)COc2ccc3ccccc3c2Br)CC(C)(C)N1] | 2-(1-bromonapthalen-2-yloxy)-N-(2,2,6,6-tetramethylpiperidin-4-yl)acetamide | |
| A17 1668-19 | 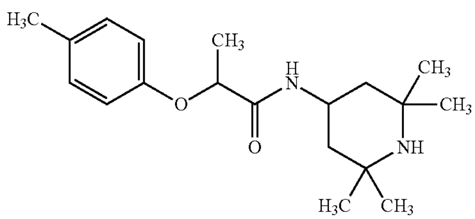 | N-(2,2,6,6-tetramethylpiperidin-4-yl)-2-(p-tolyloxy)propanamide | |
| A18 1668-20 | 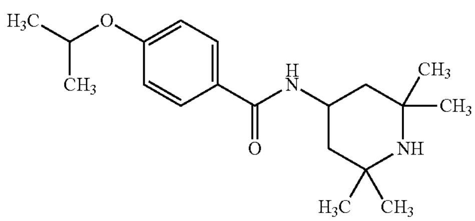 [SMILES: CC(C)Oc1ccc(C(=O)NC2CC(C)(C)NC(C)(C)C2)cc1] | 4-isopropoxy-N-(2,2,6,6-tetramethylpiperidinyl)benzamide | |
| A19 1668-21 | 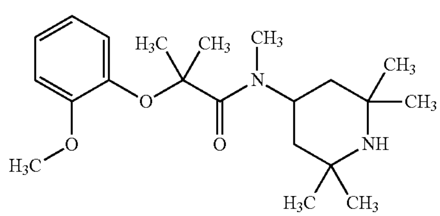 [SMILES: COc1ccccc1OC(C)(C)C(=O)N(C)C1CC(C)(C)NC(C)(C)C1] | 2-(2-methoxyphenoxy)-N,2-diimethyl-N-(2,2,6,6-tetramethylpiperidin-4-yl)propanamide; | |
| A20 1668-22 | 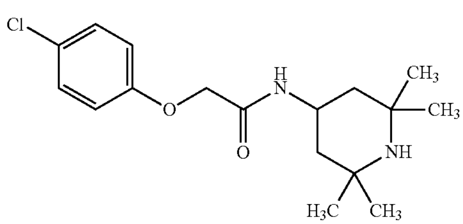 [SMILES: CC1(C)CC(NC(=O)COc2ccc(Cl)cc2)CC(C)(C)N1] | 2-(4-chlorophenoxy)-N-(2,2,6,6-tetramethylpiperidin-4-yl)acetamide | |
| A21 1668-23 | 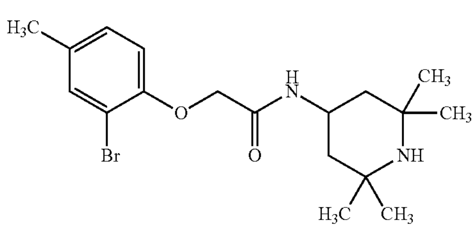 | 2-(2-bromo-4-methylphenoxy)-N-(2,2,6,6-tetramethylpiperidin-4-yl)acetamide | |

B. Quinazoline Inhibitors

| Compound No. | Structure | Name | IC50 (μM) |
|---|---|---|---|
| B1 6188-1 | 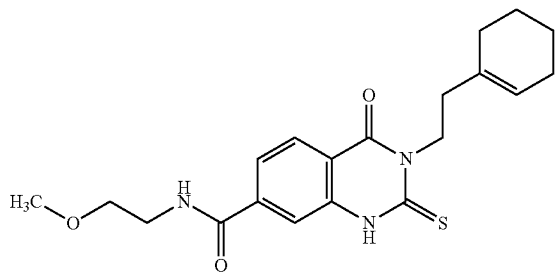 [SMILES: COCCNC(=O)c1ccc2c(=O)n(CCC3=CCCCC3)c(=S)[nH]c2c1] | 3-(2-cyclohexenylethyl)-N-(2-methoxyethyl)-4-oxo-2-thioxo-1,2,3,4-tetrahydroquinazoline-7-carboxamide | 3.3 |
| B2 6188-2 | 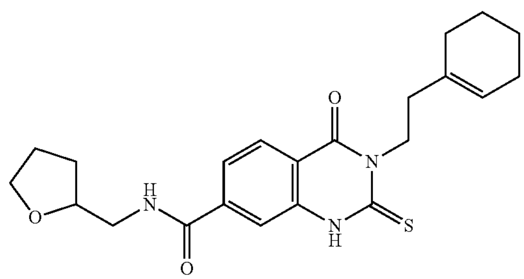 | 3-(2-cyclohexenylethyl)-4-oxo-N-((tetrahydrofuran-2-yl)methyl)-2-thioxo-1,2,3,4-tetrahydroquinazoline-7-carboxamide | |
| B3 6188-3 | 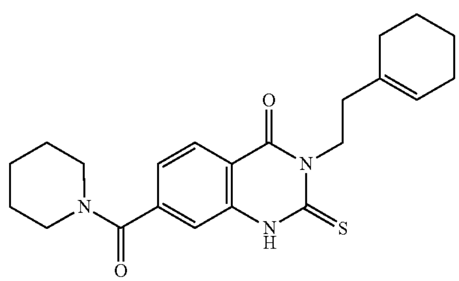 [SMILES: O=C(c1ccc2c(=O)n(CCC3=CCCCC3)c(=S)[nH]c2c1)N1CCCCC1] | 3-(2-cyclohexenylethyl)-7-piperidine-1-carbonyl)-2-thioxo-2,3-dihydroquinazolin-4(1H)-one | |
| B4 6188-4 | 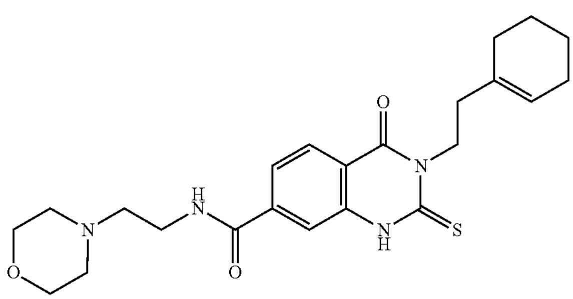 [SMILES: O=C(NCCN1CCOCC1)c1ccc2c(=O)n(CCC3=CCCCC3)c(=S)[nH]c2c1] | 3-(2-cyclohexenylethyl)-N-(2-morpholinoethyl)-4-oxo-2-thioxo-1,2,3,4-tetrahydroquinazoline-7-carboxamide | |
| B5 6188-5 | 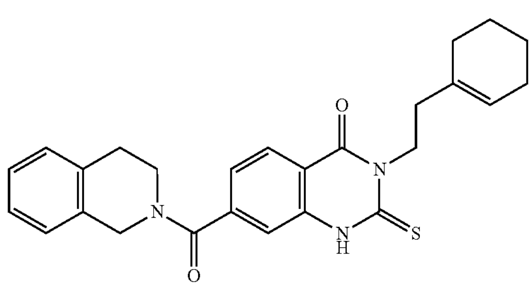 [SMILES: O=C(c1ccc2c(=O)n(CCC3=CCCCC3)c(=S)[nH]c2c1)N1CCc2ccccc2C1] | 3-(2-cyclohexenylethyl)-7-(1,2,3,4-tetrahydroisoquinoline-2-carbonyl)-2-thioxo-2,3-dihydroquinazolin-4(1H)-one | |

-continued

| Compound No. | Structure | Name | IC50 (μM) |
|---|---|---|---|
| B6 6188-6 | 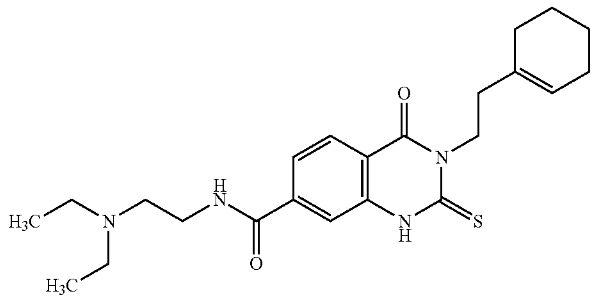 [SMILES: CCN(CC)CCNC(=O)c1ccc2c(=O)n(CCC3=CCCCC3)c(=S)[nH]c2c1] | 3-(2-cyclohexenylethyl)-N-(2-(diethylamino)ethyl)-4-oxo-2-thioxo-1,2,3,4-tetrahydroquinazoline-7-carboxamide e | |
| B7 6188-7 | 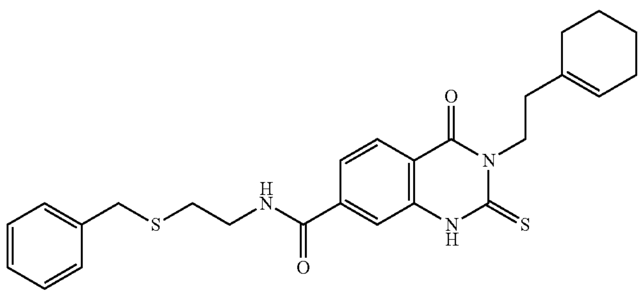 [SMILES: O=C(NCCSCc1ccccc1)c1ccc2c(=O)n(CCC3=CCCCC3)c(=S)[nH]c2c1] | N-(2-benzylthio)ethyl-3-(2-cyclohexenylethyl)-4-oxo-2-thioxo-1,2,3,4-tetrahydroquinazoline-7-carboxamide | |
| B8 6188-8 | 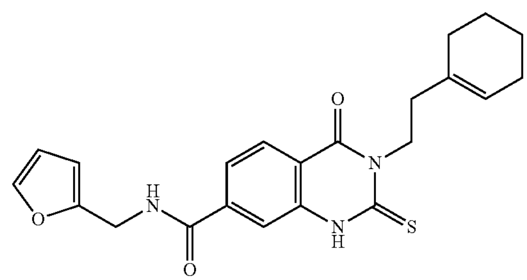 [SMILES: O=C(NCc1ccco1)c1ccc2c(=O)n(CCC3=CCCCC3)c(=S)[nH]c2c1] | 3-(2-cyclohexenylethyl)-N-(furan-2-ylmethyl)-4-oxo-2-thioxo-1,2,3,4-tetrahydroquinazoline-7-carboxamide | |
| B9 6188-10 | 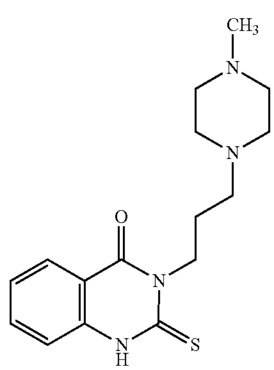 [SMILES: CN1CCN(CCCn2c(=S)[nH]c3ccccc3c2=O)CC1] | 3-(3-(4-methylpiperazin-1-yl)propyl-2-thioxo-2,3-dihydroquinazolin-4-(1H)-one | |
| B10 6188-11 | 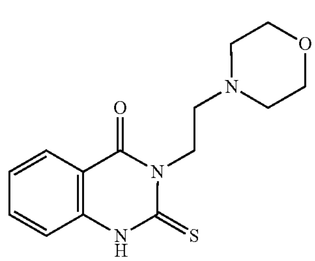 [SMILES: O=c1c2ccccc2[nH]c(=S)n1CCN1CCOCC1] | 3-(2-morpholinoethyl)-2-thioxo-2,3-dihydroquinazolin-4-(1H)-one | |

| Compound No. | Structure | Name | IC50 (µM) |
|---|---|---|---|
| B11 6188-12 | 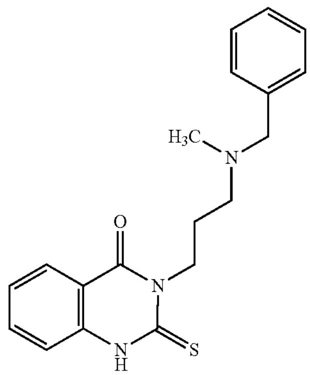 [SMILES: CN(CCCn1c(=S)[nH]c2ccccc2c1=O)Cc1ccccc1] | 3-(3-(benzyl(methyl)amino) propyl)-2-thioxo-2,3-dihydro-quinazolin-4-(1H)-one | |
| B12 6188-13 | 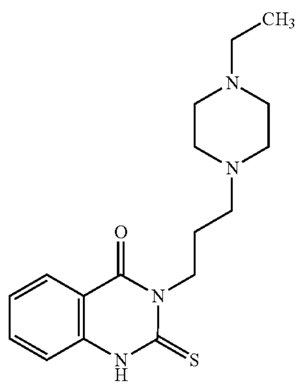 [SMILES: CCN1CCN(CCCn2c(=S)[nH]c3ccccc3c2=O)CC1] | 3-(3-(4-ethylpiperazin-1-yl)propyl)-2-thioxo-2,3-dihydroquinazolin-4-(1H)-one | 316 |
| B13 6188-14 | 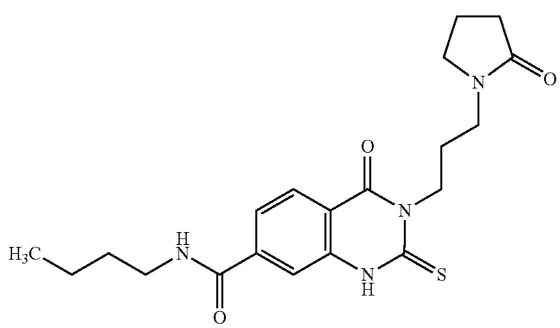 [SMILES: CCCCNC(=O)c1ccc2c(=O)n(CCCN3CCCC3=O)c(=S)[nH]c2c1] | N-butyl-4-oxo-3-(3-(2-oxopyrrolidin-1-yl)propyl)-2-thioxo-1,2,3,4-tetrahydroquinazoline-7-carboxamide | |
| B14 6188-15 | 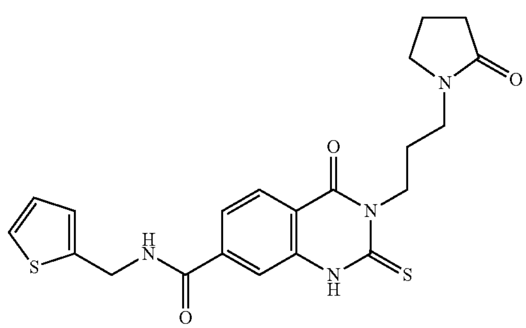 [SMILES: O=C(NCc1cccs1)c1ccc2c(=O)n(CCCN3CCCC3=O)c(=S)[nH]c2c1] | 4-oxo-3-(3-2-oxopyrrolodin-1-yl)propyl)-N-(thiophen-2-ylmethyl)-2-thioxo-1,2,3,4-tetrahydroquinazoline-7-carboxamide | |

| Compound No. | Structure | Name | IC50 (μM) |
|---|---|---|---|
| B15 6188-16 | 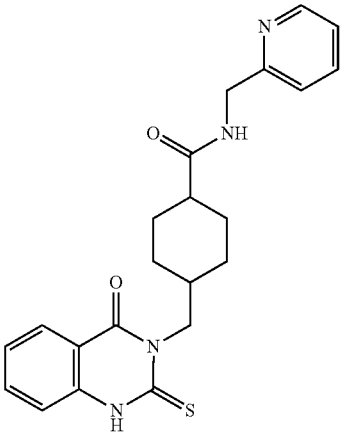 [SMILES: O=C(NCc1ccccn1)C1CCC(Cn2c(=S)[nH]c3ccccc3c2=O)CC1] | 4-((4-oxo-2-thioxo-1,2-dihydroquinazolin-3(4H)-yl)methyl)-N-(pyridin-2-ylmethyl)cyclohexanecarboxamide | |
| B16 6188-17 | 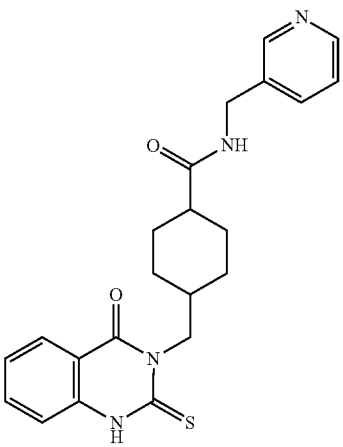 [SMILES: O=C(NCc1cccnc1)C1CCC(Cn2c(=S)[nH]c3ccccc3c2=O)CC1] | 4-((4-oxo-2-thioxo-1,2-dihydroquinazolin-3(4H)-yl)methyl)-N-(pyridin-3-ylmethyl)cyclohexanecarboxamide | |
| B17 6188-18 | 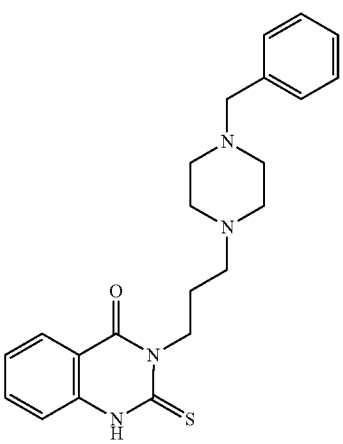 [SMILES: O=c1c2ccccc2[nH]c(=S)n1CCCN1CCN(Cc2ccccc2)CC1] | 3-(3-(4-benzylpiperazin-1-yl)propyl)-2-thioxo-2,3-dihydroquinazolin-4(1H)-one | |

-continued

| Compound No. | Structure | Name | IC50 (μM) |
|---|---|---|---|
| B18 6188-19 | 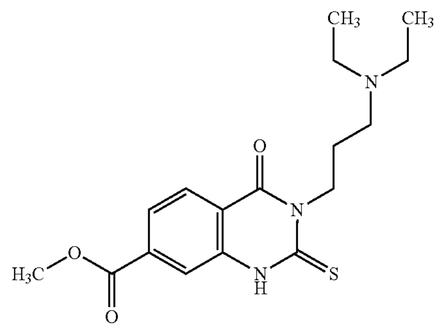 [SMILES: CCN(CC)CCCn1c(=S)[nH]c2cc(C(=O)OC)ccc2c1=O] | Methyl 3-(3-(diethylamino)propyl)-4-oxo-2-thioxo-1,2,3,4-tetrahydroquinazoline-7-carboxamide | |
| B19 6188-20 | 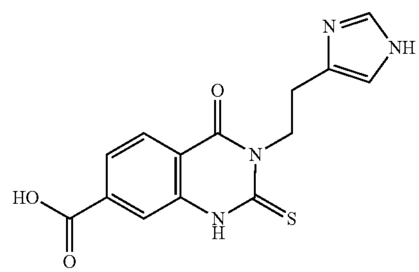 [SMILES: O=C(O)c1ccc2c(=O)n(CCc3c[nH]cn3)c(=S)[nH]c2c1] | 3-(2-(1H-imidazol-4-yl)ethyl-4-oxo-2thioxo-1,2,3,4-tetrahydroquinazoline-7-carboxamide | |
| B20 6188-21 | 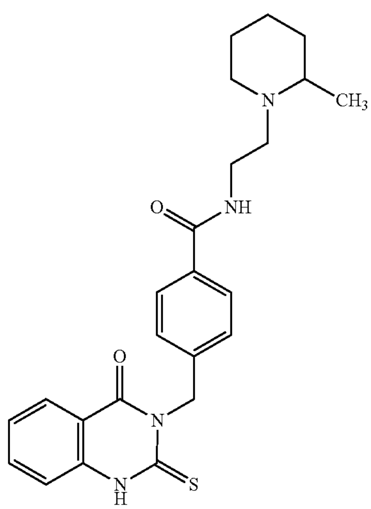 [SMILES: CC1CCCCN1CCNC(=O)c1ccc(Cn2c(=S)[nH]c3ccccc3c2=O)cc1] | N-(2-(2-methylpiperidin-4-yl)ethyl)-4-((4-oxo-2-thioxo-1,2-dihydroquinazolin-3(4H)-yl)methyl)benzamide | 398 |
| B21 6188-23 | 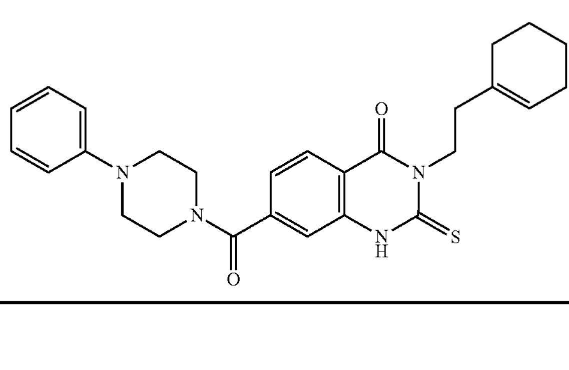 | 3-(2-cyclohexenylethyl)-7-(4-phenylpiperazine-1-carbonyl)-2-thioxo-2,3-dihydroquinazolin-4(1H)-one | |

C. Triazine Inhibitors

| Compound No. | Structure | Name | IC 50 (units) |
|---|---|---|---|
| C1 8391-1 | 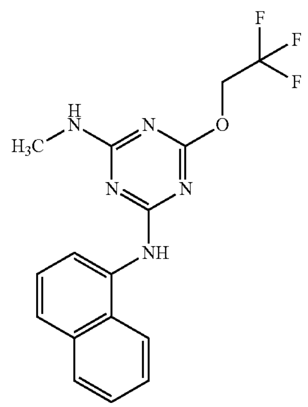 [SMILES: CNc1nc(Nc2cccc3ccccc23)nc(OCC(F)(F)F)n1] | $N^2$-methyl-$N^4$-(napthalen-1-yl)-6-(2,2,2-trifluoroethoxy)-1,3,5-triazine-2,4-diamine | |
| C2 8391-5 | 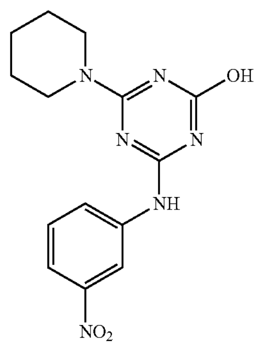 [SMILES: O=[N+]([O-])c1cccc(Nc2nc(O)nc(N3CCCCC3)n2)c1] | 4-(3-nitrophenylamino)-6-(piperidin-1-yl)-1,3,5-triazin-2-ol | |
| C3 8391-7 | 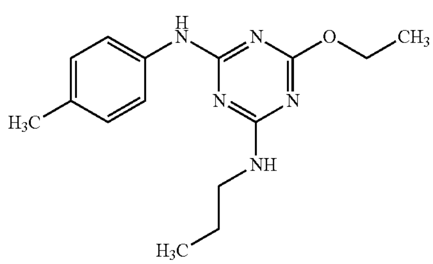 [SMILES: CCCNc1nc(Nc2ccc(C)cc2)nc(OCC)n1] | 6-ethoxy-$N^2$-propyl-$N^4$-p-tolyl-1,3,5-triazine-2,4-diamine | |
| C4 8391-8 | 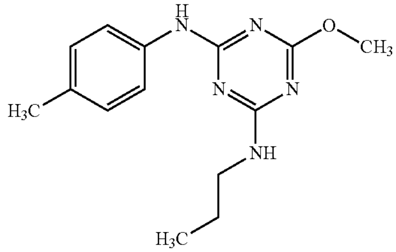 | 6-methoxy-$N^2$-propyl-$N^4$-p-tolyl-1,3,5-triazine-2,4-diamine | |

| Compound No. | Structure | Name | IC 50 (units) |
|---|---|---|---|
| C5 8391-9 | 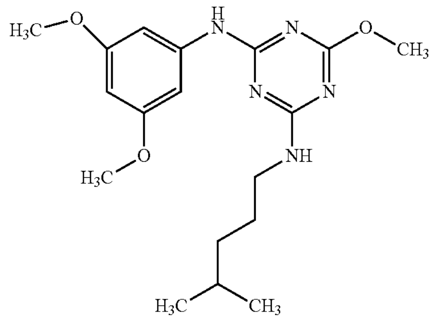 | $N^2$-(3,5-(dimethoxyphenyl)-6-methoxy-$N^4$-(4-methylpentyl)-1,3,5-triazine-2,4-diamine | |
| C6 8391-15 | 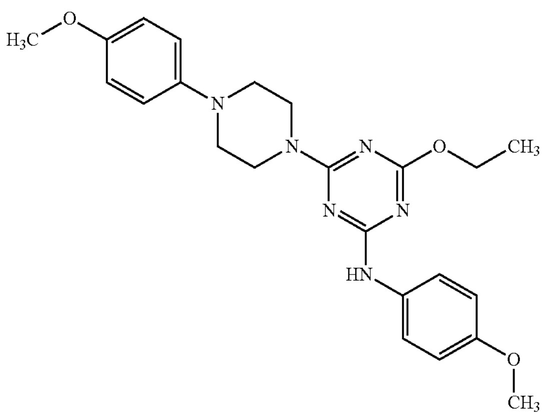 [SMILES: CCOc1nc(Nc2ccc(OC)cc2)nc(N2CCN(c3ccc(OC)cc3)CC2)n1] | 4-ethoxy-N-(4-methoxyphenyl)-6-(4-(4-methoxyphenyl)piperazin-1-yl)-1,3,5-triazine-2,4-diamine | |
| C7 8391-2 | 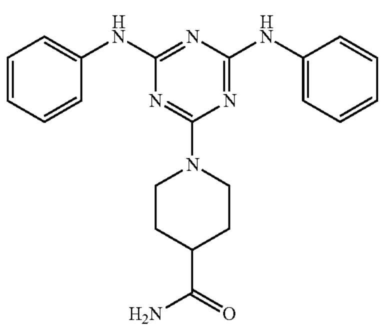 [SMILES: NC(=O)C1CCN(c2nc(Nc3ccccc3)nc(Nc3ccccc3)n2)CC1] | 1-(4,6-bisphenylamino)-1,3,5-triazin-2-yl)piperidine-4-carboxamide | |
| C8 8391-3 | 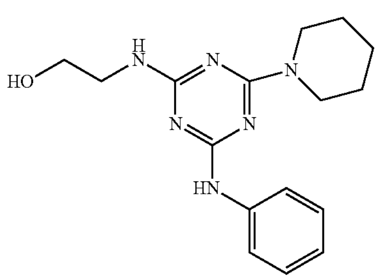 [SMILES: OCCNc1nc(Nc2ccccc2)nc(N2CCCCC2)n1] | 2-(4-phenylamino)-6-(piperidin-1-yl)-1,3,5-triazin-2-ylamino)ethanol | |

-continued

| Compound No. | Structure | Name | IC 50 (units) |
|---|---|---|---|
| C9 8391-4 | 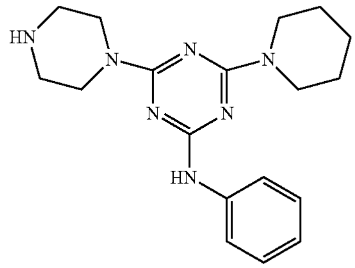 [SMILES: c1ccc(Nc2nc(N3CCCCC3)nc(N3CCNCC3)n2)cc1] | N-phenyl-4-(piperazin-1-yl)-6-(piperidin-1-yl)-1,3,5-triazin-2-amine | |
| C10 8391-6 | 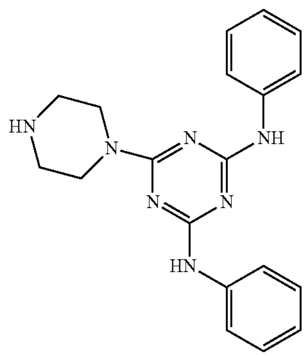 [SMILES: c1ccc(Nc2nc(Nc3ccccc3)nc(N3CCNCC3)n2)cc1] | $N^2,N^4$-diphenyl-6-(piperazin-1-yl)-1,3,5-triazine-2,4-diamine | 5.3 |
| C11 8391-11 | 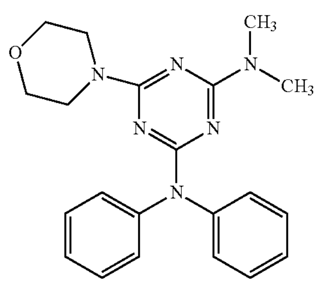 [SMILES: CN(C)c1nc(N2CCOCC2)nc(N(c2ccccc2)c2ccccc2)n1] | $N^2,N^2$-dimethyl-6-morpholino-$N^4,N^4$-diphenyl-1,3,5-triazine-2,4-diamine | |
| C12 8391-12 | 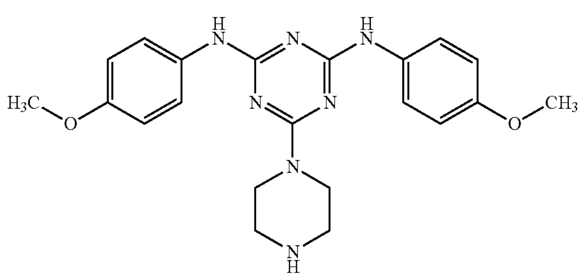 | $N^2,N^4$-bis(4-methoxyphenyl)-6-(piperazin-1-yl)-1,3,5-triazine-2,4-diamine | 355 |
| C13 8391-13 | 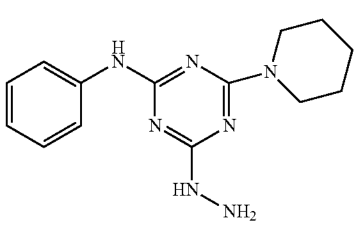 [SMILES: NNc1nc(Nc2ccccc2)nc(N2CCCCC2)n1] | 4-hydrazinyl-N-phenyl-6-(piperdin-1-yl)-1,3,5-triazin-2-amine | |

-continued

| Compound No. | Structure | Name | IC 50 (units) |
|---|---|---|---|
| C14 8391-14 | 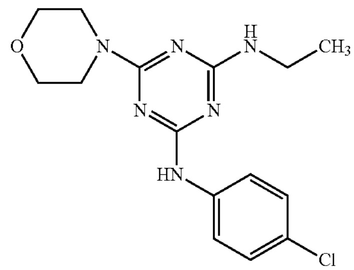 [SMILES: CCNc1nc(Nc2ccc(Cl)cc2)nc(N2CCOCC2)n1] | $N^2$-(4-chlorophenyl)-$N^4$-ethyl-6-morpholino-1,3,5-triazine-2,4-diamine | |
| C15 8391-16 | 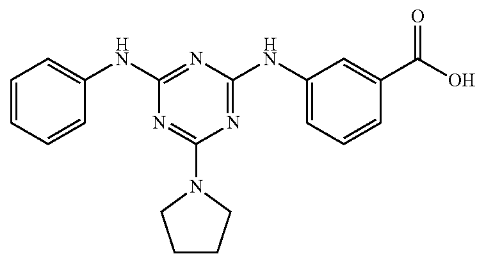 [SMILES: O=C(O)c1cccc(Nc2nc(Nc3ccccc3)nc(N3CCCC3)n2)c1] | 3-(4-(phenylamino)-6-(pyrrolidin-1-yl)-1,3,5-triazin-2-ylamino)benzoic acid | |
| C16 8391-17 | 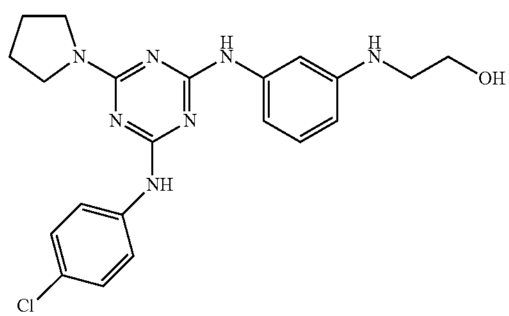 [SMILES: OCCNc1cccc(Nc2nc(Nc3ccc(Cl)cc3)nc(N3CCCC3)n2)c1] | 2-(3-(4-(4-chlorophenylamino)-6-(pyrrolidin-1-yl)-1,3,5-triazin-2-ylamino)phenylamino)ethanol | |
| C17 8391-18 | 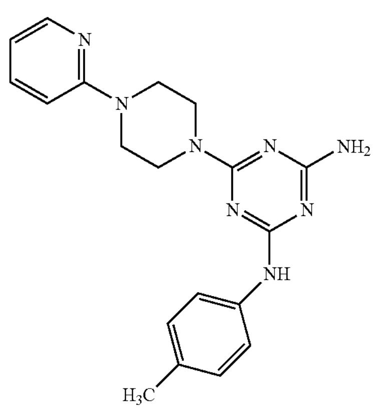 [SMILES: Cc1ccc(Nc2nc(N)nc(N3CCN(c4ccccn4)CC3)n2)cc1] | 6-(4-(pyridin-2-yl)piperazin-1-yl)-$N^2$-p-tolyl-1,3,5-triazine-2,4-diamine | |
| C18 8391-19 | 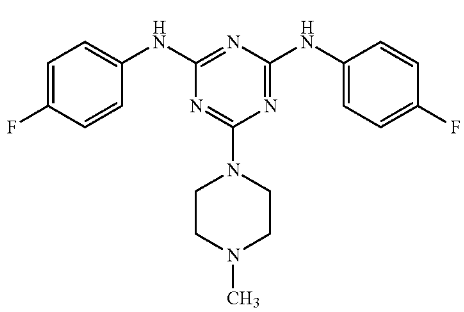 [SMILES: CN1CCN(c2nc(Nc3ccc(F)cc3)nc(Nc3ccc(F)cc3)n2)CC1] | $N^2,N^4$-bis-(4-triflourophenyl)-6-(4-methylpiperazin-1-yl)-1,3,5-triazine-2,4-diamine | |

-continued

| Compound No. | Structure | Name | IC 50 (units) |
|---|---|---|---|
| C19 8391-20 | 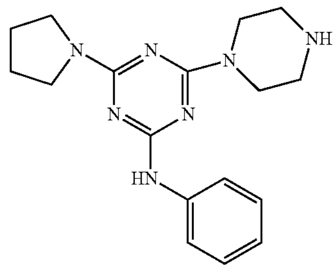 [SMILES: c1ccc(Nc2nc(N3CCCC3)nc(N3CCNCC3)n2)cc1] | N-phenyl-4-(piperazin-1-yl)-6-(pyrrolidin-1-yl)-1,3,5-triazine-2,4-diamine | |
| C20 8391-20 | 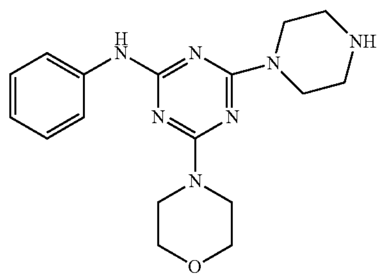 [SMILES: c1ccc(Nc2nc(N3CCNCC3)nc(N3CCOCC3)n2)cc1] | 4-morpholino-N-phenyl-6-(piperazin-1-yl)-1,3,5-triazine-2,4-diamine | |

D. Isoquinoline Inhibitors

| Compound No. | Structure | Name | IC 50 ($\mu$M) |
|---|---|---|---|
| D1 18200-4 | 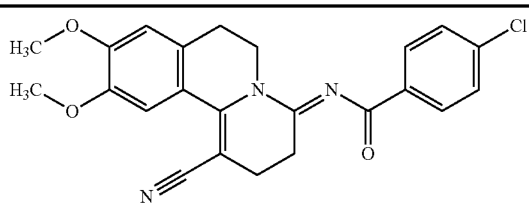 | (E)-4-chloro-N-(1-cyano-9,10-dimethoxy-6,7-dihydro-2H-pyrido[2,1-a]isoquinolin-4(3H)-ylidene)benzamide | 14 |
| D2 18200-2 | 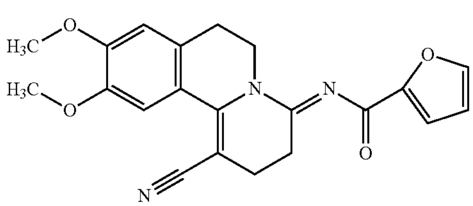 [SMILES: COc1cc2c(cc1OC)C1=C(C#N)CC/C(=N\C(=O)c3ccco3)N1CC2] | (E)-N-(1-cyano-9,10-dimethoxy-6,7-dihydro-2H-pyrido[2,1-a]isoquinolin-4(3H)-ylidene)furan-2-carboxamide | |
| D3 18200-1 | 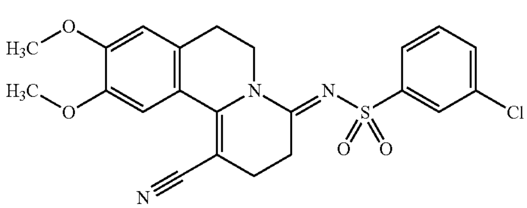 [SMILES: COc1cc2c(cc1OC)C1=C(C#N)CC/C(=N\S(=O)(=O)c3cccc(Cl)c3)N1CC2] | (E)-3-chloro-N-(1-cyano-9,10-dimethoxy-6,7-dihydro-2H-pyrido[2,1-a]isoquinolin-4(3H)-ylidene)benznesulfonamide | |
| D4 18200-3 | 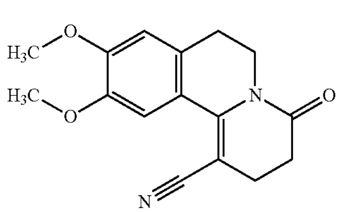 [SMILES: COc1cc2c(cc1OC)C1=C(C#N)CCC(=O)N1CC2] | 9,10-dimethoxy-4-oxo-3,4,6,7-tetrahydro-2H-pyrido[2,1-a]isoquinoline-1-carbonitrile | |

E. Other Small Molecule Inhibitors

| Compound No. | Structure | Name | IC 50 (μM) |
|---|---|---|---|
| E1 3643 | 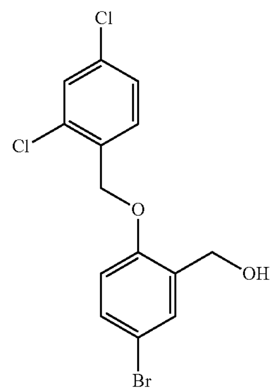 [SMILES: OCc1cc(Br)ccc1OCc1ccc(Cl)cc1Cl] | (5-bromo-2-(2,4-dichlorobenzyloxy)phenyl)methanol | |
| E2 2491 | 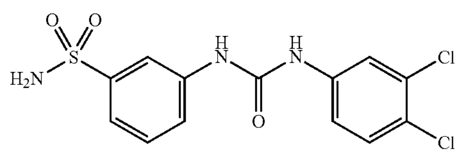 [SMILES: NS(=O)(=O)c1cccc(NC(=O)Nc2ccc(Cl)c(Cl)c2)c1] | 3-(3-(3,4-dichlorophenyl)ureido)benzenesulfonamide | 75 |
| E3 12204 | 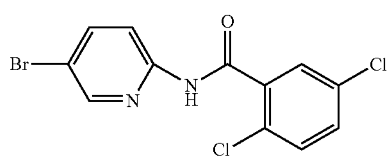 [SMILES: O=C(Nc1ccc(Br)cn1)c1cc(Cl)ccc1Cl] | N-(5-bromopyridin-2-yl)-2,5-dichlorobenzamide | |
| E4 2493 | 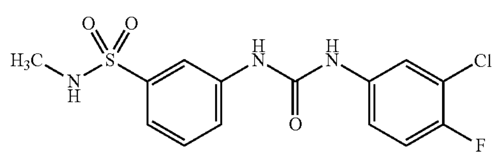 [SMILES: CNS(=O)(=O)c1cccc(NC(=O)Nc2ccc(F)c(Cl)c2)c1] | 3-(3-(3-chloro-4-fluorophenyl)ureido)-N-methylbenzenesulfonamide | |
| E5 831 | 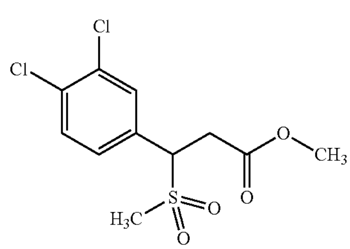 [SMILES: COC(=O)CC(c1ccc(Cl)c(Cl)c1)S(C)(=O)=O] | methyl 3-(3,4-dichlorophenyl)-3-(methylsulfonyl)propanoate | |
| E6 12327 | 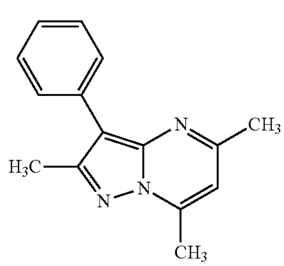 [SMILES: Cc1cc(C)n2nc(C)c(-c3ccccc3)c2n1] | 2,5,7-trimethyl-3-phenylpyrazolo[1,5-a]pyrimidine | |

-continued

| Compound No. | Structure | Name | IC 50 (μM) |
|---|---|---|---|
| E7 2725 | 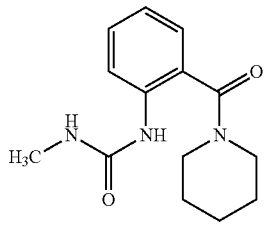 [SMILES: CNC(=O)Nc1ccccc1C(=O)N1CCCCC1] | 1-methyl-3-(2-(piperidine-1-carbonyl)phenyl)urea | |
| E8 9324 | 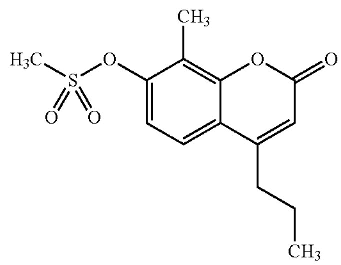 [SMILES: CCCc1cc(=O)oc2c(C)c(OS(C)(=O)=O)ccc12] | 8-methyl-2-oxo-4-propyl-2H-chromen-7-yl methanesulfonate | |
| E9 12542 | 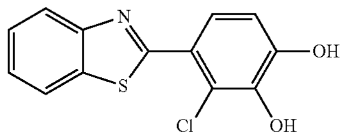 [SMILES: Oc1ccc(-c2nc3ccccc3s2)c(Cl)c1O] | 4-(benzo(d)thiazol-2-yl)-3-chlorobenzene-1,2-diol | |
| E10 12745 | 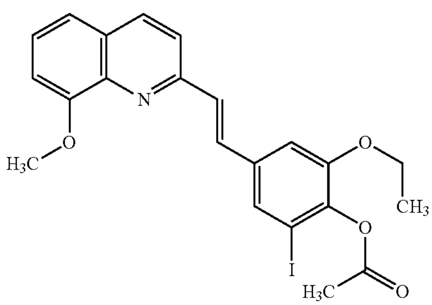 [SMILES: CCOc1cc(/C=C/c2ccc3cccc(OC)c3n2)cc(I)c1OC(C)=O] | (E)-2-(3-ethoxy-6-iodo-4(2-(8-methoxyquinolin-2-yl)vinyl)phenyl acetate | |
| E11 12744 | 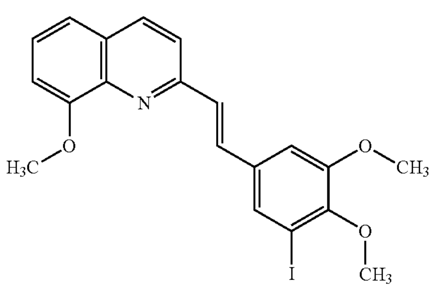 [SMILES: COc1cc(/C=C/c2ccc3cccc(OC)c3n2)cc(I)c1OC] | (E)-2-(3-methoxy-5-iodo-4-methoxystyryl)-8-methoxyquinoline | |
| E12 14094 | 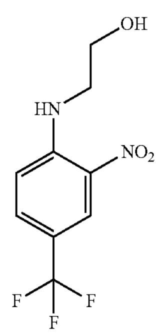 [SMILES: O=[N+]([O-])c1cc(C(F)(F)F)ccc1NCCO] | 2-(2-nitro-4-(trifluoromethyl)phenylamino)ethanol | |

| Compound No. | Structure | Name | IC 50 (μM) |
|---|---|---|---|
| E13 1668-18 | 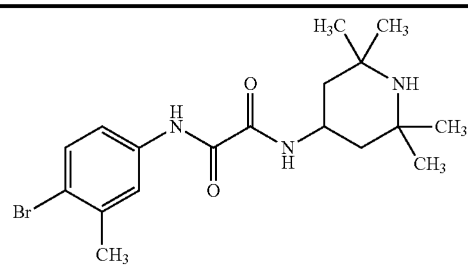 | N$^1$-(4-bromo-3-methylphenyl)-N$^2$-(2,2,6,6-tetramethylpiperidin-4-yl)oxalimide | |
| E14 2712 | 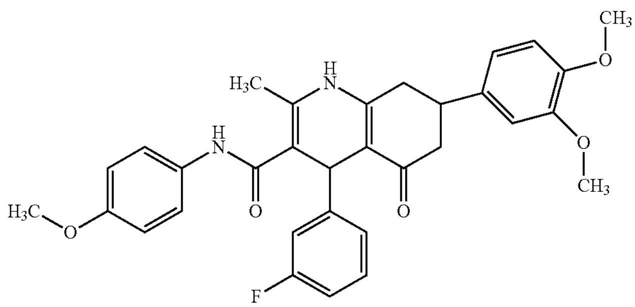 | 7-(3,4-dimethoxyphenyl)-4-(3-fluorophenyl)-N-(4-methoxyphenyl)-2-methyl-5-oxo-1,4,5,6,7,8-hexahydroquinoline-3-carboxamide | |
| E15 16286 | 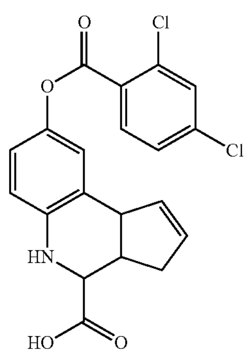 [SMILES: O=C(Oc1ccc2c(c1)C1C=CCC1C(C(=O)O)N2)c1ccc(Cl)cc1Cl] | 8-(2,4-dichlorobenzyloxy)-3a,4,5,9b-tetrahydro-3H-cyclopenta[c]quinoline-4-carboxylic acid | 18 |
| SAB-157 | 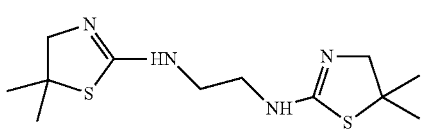 | N1,N2-bis(5,5-dimethyl-4,5-dihydrothiazol-2-yl)ethane-1,2-diamine | |

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:

1. A method of treating HIV/AIDS disease in a patient in need thereof, said method comprising administering a therapeutically effective amount of one or more compounds of formula (VII):

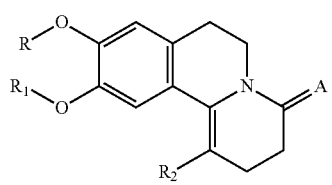

(VII)

Wherein:
R$_2$ is —CN;
R and R$_1$ is C$_1$-C$_4$ alkyl;
A is O, or N—X—R"; wherein X is —C=O, or —SO$_2$—;
R" is aryl, or heteroaryl; and
pharmaceutically acceptable salts, solvates, prodrugs, polymorphs, stereoisomers, and tautomers thereof.

2. The method of claim 1, wherein said compound of formula VII is selected from the group consisting of 18200-1, 18200-2, 18200-3 and 18200-4.

3. The method according to claim 1, wherein said compound of formula VII is 18200-3.

4. A method of treating HIV/AIDS by inhibiting interaction of one or more viral proteins with human tRNA in a subject in need thereof: said method comprising administration of a therapeutically effective amount of a compound that has a preferential specificity and/or binding affinity to human tRNA$_3$Lys, wherein the compound having preferential specificity and/or binding affinity to human tRNA$_3$Lys is a compound of formula (VII) as set forth in claim 1.

5. The method of claim 4, wherein said compound of formula VII is selected from the group consisting of 18200-1, 18200-2, 18200-3 and 18200-4.

6. The method according to claim 4, wherein said compound of formula VII is 18200-3.

7. A method of inhibiting viral preparation or viral recruitment of tRNA$_3$Lys comprising contacting said tRNA$_3$Lys with the compound of formula (VII) as set forth in claim 1, in an amount effective to inhibit viral preparation or viral recruitment of tRNA$_3$Lys.

8. The method of claim 7, wherein said compound of formula VII is selected from the group consisting of 18200-1, 18200-2, 18200-3 and 18200-4.

9. The method of claim 7, wherein said compound of formula VII is 18200-3.

10. The method according to claim 7, wherein a patient in need thereof is administered the compound of formula (VII) as set forth in claim 1.

* * * * *

SEQUENCE LISTING

<160> NUMBER OF SEQ ID NOS: 21

<210> SEQ ID NO 1
<211> LENGTH: 15
<212> TYPE: PRT
<213> ORGANISM: Artificial Sequence
<220> FEATURE:
<223> OTHER INFORMATION: hASL LYS3 binding peptide

<400> SEQUENCE: 1

Phe Ser Val Ser Phe Pro Ser Leu Pro Ala Pro Pro Asp Arg Ser
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: hASL LYS3 binding peptide

<400> SEQUENCE: 2

Gly Arg Val Thr Tyr Tyr Ser Cys Gly Val Ser Leu Leu Phe Gln
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: hASL LYS3 binding peptide

<400> SEQUENCE: 3

Ala Gly Pro Val Pro Leu His Ser Leu Ser Tyr Tyr Tyr Asn Gln
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: hASL LYS3 binding peptide

<400> SEQUENCE: 4

Arg Ala Val Met Thr Val Val Trp Pro Val Ser Phe Ala Gly Phe
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: hASL LYS3 binding peptide

<400> SEQUENCE: 5

Arg Val Thr His His Ala Phe Leu Gly Ala His Arg Thr Val Gly
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: hASL LYS3 binding peptide

<400> SEQUENCE: 6

Pro Ala Val Ala Ser Thr Ser Ser Leu Ile Ile Asp Gly Pro Phe
1               5                   10                  15

```
<210> SEQ ID NO 7
<211> LENGTH: 15
<212> TYPE: PRT
<213> ORGANISM: Artificial Sequence
<220> FEATURE:
<223> OTHER INFORMATION: hASL LYS3 binding peptide

<400> SEQUENCE: 7

Pro Lys Ala Phe Gln Tyr Gly Gly Arg Ala Val Gly Gly Leu Trp
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: hASL LYS3 binding peptide

<400> SEQUENCE: 8

Ala Ala His Val Ser Glu His Tyr Val Ser Gly Ser Leu Arg Pro
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: hASL LYS3 binding peptide

<400> SEQUENCE: 9

Ala Ser Val Gly Pro Ala Pro Trp Ala Met Thr Pro Pro Val Ser
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: hASL LYS3 binding peptide

<400> SEQUENCE: 10

Ala Pro Ala Leu Trp Tyr Pro Trp Arg Ser Leu Leu Pro Leu Tyr
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: hASL LYS3 binding peptide

<400> SEQUENCE: 11

Ala Ser Leu His Pro Val Pro Lys Thr Trp Phe Phe Leu Leu Ser
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: modified tRNA binding peptide

<400> SEQUENCE: 12

Trp Ser His Ser Arg Asn Thr Ala Asp Val Pro Val Ser Met Leu
1               5                   10                  15
```

```
<210> SEQ ID NO 13
<211> LENGTH: 15
<212> TYPE: PRT
<213> ORGANISM: Artificial Sequence
<220> FEATURE:
<223> OTHER INFORMATION: hASL LYS3 binding peptide

<400> SEQUENCE: 13

His Arg Gly Tyr Cys Arg Asp Arg Trp Asn Cys Gly Glu Tyr Phe
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: hASL LYS3 binding peptide

<400> SEQUENCE: 14

Pro His Arg Gln Cys Ser Ala Pro Ala Lys Ser Cys Lys Ile Leu Pro
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: hASL LYS3 binding peptide

<400> SEQUENCE: 15

Thr Leu Pro Ala Cys His Glu Leu Pro Lys His Cys Lys Arg Arg Gly
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: hASL LYS3 binding peptide

<400> SEQUENCE: 16

Thr Leu Pro Ala Cys His Glu Leu Pro Lys His Cys Asn Glu Ala Arg
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: hASL LYS3 binding peptide

<400> SEQUENCE: 17

Asn Gly Pro Glu Cys Asn Ala Tyr Met Val Arg Cys Arg Gly Tyr His
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: hASL LYS3 binding peptide

<400> SEQUENCE: 18

Gly Asn Ser Asn Cys Pro Met Leu Asn Glu Gln Cys Pro Trp Gln Asp
1               5                   10                  15
```

```
<210> SEQ ID NO 19
<211> LENGTH: 16
<212> TYPE: PRT
<213> ORGANISM: Artificial Sequence
<220> FEATURE:
<223> OTHER INFORMATION: hASL LYS3 binding peptide

<400> SEQUENCE: 19

His Thr Glu Thr Cys Ile Asn Ile Arg Asn Thr Cys Thr Thr Val Ala
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: hASL LYS3 binding peptide

<400> SEQUENCE: 20

Leu Lys Leu Pro Cys Lys Ile Thr Ile Asn Asn Cys Gln Leu Ala Gly
1               5                   10                  15

<210> SEQ ID NO 21
<211> LENGTH: 17
<212> TYPE: RNA
<213> ORGANISM: Artificial Sequence
<220> FEATURE:
<223> OTHER INFORMATION: Synthetic modified target hASL Lys3 sequence
<220> FEATURE:
<221> NAME/KEY: misc_feature
<222> LOCATION: (8)..(8)
<223> OTHER INFORMATION: May be 5-methoxycarbonylmethyl-2-thiouridine
<220> FEATURE:
<221> NAME/KEY: misc_feature
<222> LOCATION: (11)..(11)
<223> OTHER INFORMATION: May be 2-methylthio-N6-
      threonylcarbamoyladenosine
<220> FEATURE:
<221> NAME/KEY: misc_feature
<222> LOCATION: (13)..(13)
<223> OTHER INFORMATION: May be pseudouridine

<400> SEQUENCE: 21
gcagacunuu nancugc                                              17
```